US008512943B2

(12) United States Patent
Nel

(10) Patent No.: US 8,512,943 B2
(45) Date of Patent: Aug. 20, 2013

(54) ACCESSING THE TOXIC POTENTIAL OF NANOMATERIALS

(75) Inventor: Andre E. Nel, Sherman Oaks, CA (US)

(73) Assignee: The Regents of the University of California, Oakland, CA (US)

(*) Notice: Subject to any disclaimer, the term of this patent is extended or adjusted under 35 U.S.C. 154(b) by 1015 days.

(21) Appl. No.: 12/095,902

(22) PCT Filed: Dec. 6, 2006

(86) PCT No.: PCT/US2006/061685
§ 371 (c)(1),
(2), (4) Date: Jun. 2, 2008

(87) PCT Pub. No.: WO2008/010843
PCT Pub. Date: Jan. 24, 2008

(65) Prior Publication Data
US 2008/0295187 A1 Nov. 27, 2008

Related U.S. Application Data

(60) Provisional application No. 60/749,269, filed on Dec. 9, 2005.

(51) Int. Cl.
*C12Q 1/00* (2006.01)
*C12Q 1/68* (2006.01)
(52) U.S. Cl.
USPC .................................................. 435/4; 435/6.1
(58) Field of Classification Search
None
See application file for complete search history.

(56) References Cited

PUBLICATIONS

Hussain et al. 2005. In vitro toxicity of nanoparticles in BRL 3A rat liver cells. Toxicology in Vitro, vol. 19, pp. 975-983.*
Wilson et al., Interactions between Ultrafine Particles and Transition Metals in Vivo and in Vitro, Toxicology and Applied Pharmacology 184, 172-179 (2002).*
Xiao et al., Use of Proteomics to Demonstrate a Hierarchical Oxidative Stress Response to Diesel Exhaust Particle Chemicals in a Macrophage Cell Line, The Journal of Biological Chemistry vol. 278, No. 50, Issue of Dec. 12, pp. 50781-50790, 2003.*
Hiura et al., The Role of a Mitochondrial Pathway in the Induction of Apoptosis by Chemicals Extracted from Diesel Exhaust Particles, J Immunol 2000;165;2703-2711.*
Li et al., Ultrafine Particulate Pollutants Induce Oxidative Stress and Mitochondrial Damage, Environmental Health Perspectives, vol. 111, No. 4, Apr. 2003.*
Stone et al., The role of oxidative stress in the prolonged inhibitory efect of ultrafine carbon black on epithelial cell function, Toxicology in vitro 12 (1998) 649-659.*
Donaldson et al., Oxidative Stress and Calcium Signaling in the Adverse Effects of Environmental Particles (PM10), Free Radical Biology & Medicine, vol. 34, No. 11, pp. 1369-1382, 2003.*

(Continued)

*Primary Examiner* — James Ketter
*Assistant Examiner* — Reza Ghafoorian
(74) *Attorney, Agent, or Firm* — K&L Gates LLP; Louis C. Cullman; Michelle Glasky Bergman

(57) ABSTRACT

A method based is provided for determining the toxicity of engineered nanomaterials (NM). The method comprises in vitro assays for oxidative stress associated with exposure to engineered NM, which comprise assays for: reactive oxygen species production; phase II and glutathione antioxidant molecule expression; activation of MAP and NF-kappa B kinase signaling cascades; production of cytokines, chemokines and adhesion molecules; mitochondrial perturbation and apoptosis; and cellular uptake and subcellular localization of the NM. The method further comprises in vivo assays for oxidative stress in subjects exposed to NM.

20 Claims, 23 Drawing Sheets

(56) References Cited

PUBLICATIONS

Hashimnoto et al., Diesel Exhaust Particles Activate p38 MAP Kinase to Produce Interleukin 8 and RANTES by Human Bronchial Epithelial Cells and N-Acetylcysteine Attenuates p38 MAP Kinase Activation, Am J Respir Crit Care Med vol. 161. pp. 280-285, 2000.*
Becker et al., Regulation of cytokine production in human alveolar macrophages and airway epithelial cells in response to ambient air pollution particles: Further mechanistic studies, Toxicology and Applied Pharmacology 207 (2005) S269-S275.*
Knaapen et al., Inhaled Particles and Lung Cancer. Part A: Mechanisms, Int. J. Cancer: 109, 799-809 (2004).*
Mirsalis et al., Transgenic animal models for detection of in vivo mutations, Annu Rev Pharmacol Toxicol. 1995;35:145-64.*
Methy et al., Differential MnSOD and HO-1 expression in cerebral endothelial cells in response to sublethal oxidative stress, Brain Research 1003 (2004) 151-158.*
Oberdorster et al., Principles for characterizing the potential human health effects from exposure to nanomaterials: elements of a screening strategy, Particle and Fibre Toxicology 2005, 2:8.*
Nantional Institute of Health publication, Guidance Document on Using In Vitro to Estimate In Vivo Starting Doses for Acute Toxicity, National Institute of Environmental Health Sciences, NIH, Aug. 2001 NIH Publication No. 01-4500.*
Donaldson et al, Ultrafine Particles, Occup Environ Med, 2001, 211-216, 58, Napier University.
Boussif et al, A versatile vector for gene and oligonucleotide transfer into cells in culture and in vivo: Polyethylenimine, Biochemistry, 1995, 7297-7301, vol. 92, Proc. Natl. Acad. Sci.
Li et al, Ultrafine Particulate Pollutants Induce Oxidative Stress and Mitochondrial Damage, Environmental Health Perspectives, 2003, 455, vol. 111, No. 4, Department of Medicine, University of California, Los Angeles.
Stone et al, Signs of stress, Nature Nanotechnology, 2006, 23, vol. 1, Nature Publishing Group.
Xia et al, Comparison of the Abilities of Ambient and Manufactured Nanoparticles to Induce Cellular Toxicity According to an Oxidative Stress Paradigm, Nano Letters, 2006, American Chemical Society.
Xiao et al, Use of proteomics to Demonstrate a Hierarchical Oxidative Stress Response to Diesel Exhaust Particle Chemicals in a Macrophage Cell Line, The Journal of Biological Chemistry, 2003, 50781-50790, vol. 278, No. 50, The American Society for Biochemistry and Molecular Biology, Inc.
Shvedova et al, Unusual inflammatory and fibrogenic pulmonary responses to single-walled carbon nanotubes in mice, American Journal of Physiology—Lung Cellular and Molecular Physiology, 2005, 698-708, 289, American Physiological Society.
Tietze, Enzymic Method for Quantitative Determination of Nanogram Amounts of Total and Oxidized Glutathione: Applications to Mammalian Blood and Other Tissues, Analytical Biochemistry, 1969, 502-522, 27, National Institute of Arthritis and Metabolic Diseases.
Withey et al, Ultra-high redox enzyme signal transduction using highly ordered carbon nanotube array electrodes, Biosensors and Bioelectronics, 2006, 1560-1565, 21, Elsevier.
Yeh et al, Nanowiring of a redox enzyme by metallized peptides, Biosensors and Bioelectronics, 2005, 973-978, 21, Elsevier.
Contag et al, In Vivo Patterns of Heme Oxygenase-1 Transcription, Journal of Perinatology, 2001, S119-S124, 21, Nature Publishing Group.
Pickering et al, Fullerol-Sensitized Production of Reactive Oxygen Species in Aqueous Solution, Environmental Science & Technology, 2005, 1359-1365, vol. 39, No. 5, American Chemical Society.
Yang et al, In Vitro Growth and Differentiation of Human Kidney Tubular Cells on a Basement Membrane Substrate, In Vitro Cellular & Developmental Biology, 1987, 34, vol. 23, No. 1, Tissue Culture Association, Inc.
Colvin, The potential environmental impact of engineered nanomaterials, Nature Biotechnology, 2003, 1166, vol. 21, No. 10, Departments of Chemistry and Chemical Engineering, Center for Biological and Environmental Nanotechnology.

* cited by examiner

FIG. 17A
FIG. 17B
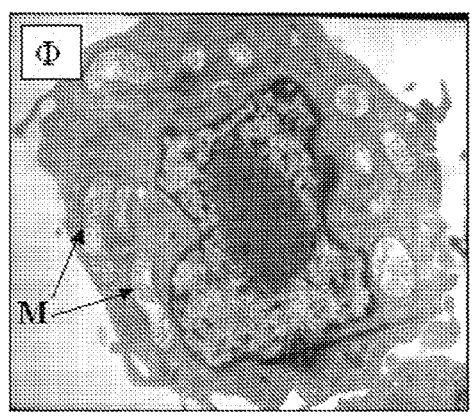
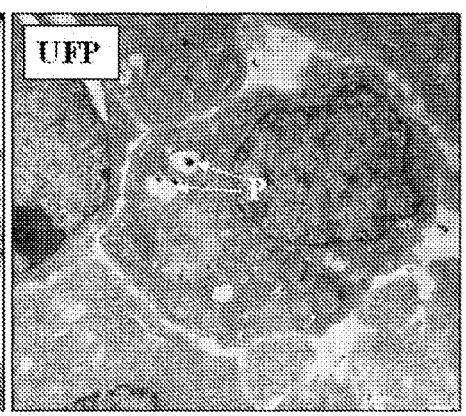
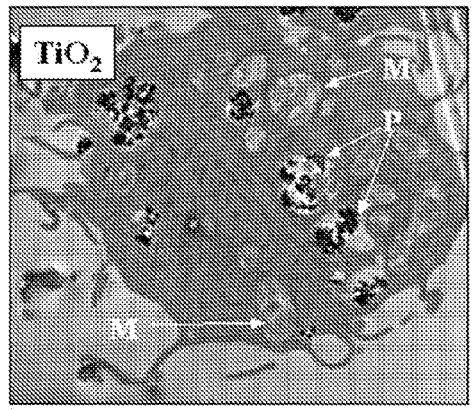
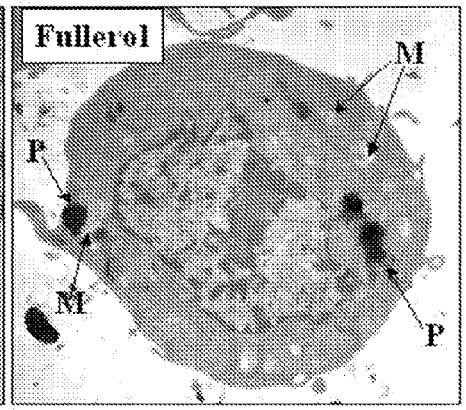
FIG. 17C
FIG. 17D

ACCESSING THE TOXIC POTENTIAL OF NANOMATERIALS

CROSS-REFERENCE TO RELATED APPLICATIONS

The present application claims the benefit under 35 U.S.C. §119(e) to U.S. Provisional Patent Application No. 60/749,269, filed Dec. 9, 2005.

STATEMENT REGARDING FEDERALLY SPONSORED RESEARCH OR DEVELOPMENT

This invention was made with United States Government support of Grant No. R82735201, awarded by the Environmental Protection Agency and Grant Nos. AI50495, ES10553, ES13432 and ES12053 awarded by the National Institutes of Health. The United States Government has certain rights in this invention.

FIELD OF THE INVENTION

The present invention relates to a method for detecting the presence and level of toxic compounds in solid materials with an aspect diameter of 100 nm or less. More particularly, the present invention relates to a method of detecting the toxicity of nanoparticles and engineered nanomaterials.

BACKGROUND OF THE INVENTION

By some estimates, nanotechnology promises to far exceed the impact of the Industrial Revolution and is projected to become a $1 trillion market by 2015. Engineered nanomaterials (NM) are already being used in sporting goods, tires, stain-resistant clothing, sunscreens, cosmetics and electronics and will also be utilized increasingly in medicine for purposes of diagnosis, imaging, and drug delivery.

Engineered nanomaterials are structures wherein the size of at least one dimension is 100 nanometer (nm) or less. The unique physicochemical properties of nanomaterials, such as engineered nanoparticles (NP), are attributable to their small size, large surface area, chemical composition, surface reactivity, surface charge, shape and media interactions. Although impressive from the perspective of material science, the novel properties of NM may lead to adverse biological effects, with the potential to create toxicity. Indeed, some studies have shown that NM can exert toxic effects and could pose hazards to humans and the environment (Service R F, Science 304: 1732, 2004; Colvin V L, Nat Biotech 21:1166, 2003; Donaldson K, et al., Occup Environ Med 58:211, 2001; Oberdörster G, et al, Environ Health Perspect 113:823, 2005; The Royal Society. Nanoscience and nanotechnologies: Opportunities and uncertainties. www.royalsoc.ac.uk, July 2004 report). sed to NM.

Moreover, some NM, such as nanoparticles, readily travel throughout the body, deposit in target organs, penetrate cell membranes, lodge in mitochondria, and may trigger injurious responses. There is almost unanimous opinion among proponents and skeptics alike that the full potential of nanotechnology requires attention to safety issues. Environmental activists have called for a worldwide moratorium on NM research and marketing until protocols are in place to ensure worker safety.

While the properties of nanomaterials could necessitate a novel investigative approach to assess their hazard potential, research into air pollution and mineral dust particles has established a scientific basis for assessing lung and cardiovascular injury by inhaled particles. This includes evidence that ambient ultrafine particles (particulate matter with physical diameters <100 nm) induce reactive oxygen species (ROS), oxidative stress and inflammation in the lung and vasculature. Likewise, occupational exposure to quartz and mineral dust particles (e.g., coal and silicates) induces oxidative injury, inflammation, fibrosis, and cytotoxicity in the lung. Tissue and cell culture analysis support the in vivo outcomes, pointing to the role of ROS and oxidative stress in the generation of pro-inflammatory responses and cytotoxic effects. Taken together, these studies indicate that their small size, large surface area, chemical composition and ability to generate ROS play a key role in the ability of ambient NP to induce lung injury.

Although the heterogeneous characteristics of ambient ultrafine particles (UFP) are very different from the homogeneous composition of manufactured NP, the limited data on manufactured particles indicate that ROS production is also a key mechanism of toxicity. For instance, water soluble fullerenes induce $O_2$ anions, lipid peroxidation, and cytotoxicity. Production of ROS, lipid peroxidation and the generation of pro-inflammatory responses have also been described in tissue culture and animal studies that addressed the potential toxicity of metal oxide particles (e.g., $TiO_2$) and carbon nanotubes. This suggests that an investigation into the mechanisms of ROS production and their biological consequences could serve as a paradigm for investigating NP toxicity.

Oxidative stress is a state of redox disequilibrium in which ROS production overwhelms the antioxidant defense capacity of the cell, thereby leading to adverse biological consequences. Oxidative stress is often expressed in terms of the glutathione (GSH) to glutathione disulfide (GSSG) ratio in the cell. Not only does the GSH/GSSG redox couple serve as the chief homeostatic regulator of cellular redox balance but also functions as a sensor that triggers additional cellular responses which, depending on the rate and level of decline, could present as protective or injurious responses. The hierarchical oxidative stress model posits that minor levels of oxidative stress induce protective effects that may yield to more damaging effects at higher levels of oxidative stress. The protective cellular effects are regulated by the transcription factor, nuclear factor, erythroid 2-related factor 2 (Nrf2), which leads to transcriptional activation of >200 antioxidant and detoxification enzymes collectively known as the phase II response. Examples of phase II enzymes include heme oxygenase 1 (HO-1), glutathione-S-transferase (GST) isoenzymes, NADPH quinone oxidoreductase (NQO1), catalase, superoxide dismutase isoenzymes, glutathione peroxidase (GPx) and glucoronosyltransferase (UGT). Defects or aberrancy in this protective pathway could determine the susceptibility to particle-induced oxidant injury, e.g., the exacerbation of allergic inflammation and asthma by exposure to diesel exhaust particles (DEP). Should these protective responses fail to lead to adequate protection, a further increase in ROS production can result in pro-inflammatory and cytotoxic effects. Pro-inflammatory effects are mediated by the redox-sensitive MAP kinase and NF-kappa B cascades that lead to the expression of cytokines, chemokines and adhesion molecules. In contrast, cytotoxic effects are mediated by mitochondria, which are capable of releasing pro-apoptotic factors. Several types of NP have the capacity to target mitochondria directly.

Despite the intense interest in nanomaterial safety, no comprehensive test paradigm has been developed to compare the toxicity of different nanomaterials. Therefore there exists an urgent need to establish principles and test procedures to ensure the safe manufacturing and use of nanomaterials.

SUMMARY OF THE INVENTION

The present invention provides methods to assess the potential adverse biological effects of nanomaterials. Specifically, the generation of reactive oxygen species (ROS) and oxidative injury provides means for quantitative measures of nanomaterial toxicological effects.

In one embodiment of present invention, a method is provided for determining the toxicity of nanomaterials comprising (a) providing a culture of cells; (b) adding thereto a quantity of nanomaterials; (c) maintaining the culture for a period of time; and (d) performing on the cells a plurality of assays for oxidative stress, the assays selected from the group of assays probing for: (i) reactive oxygen species (ROS) production; (ii) phase II antioxidant molecule expression; (iii) activation of proinflammatory cascades; (vi) mitochondrial perturbation and apoptosis; and cellular uptake and subcellular localization of the nanoparticles; wherein the results of said assays predict the toxicity of said nanomaterials.

In another embodiment, the cells are selected from the group consisting of macrophages, epithelial cells, endothelial cells, keratinocytes, neuronal cells, kidney cells, liver cells, antigen presenting cells and *Salmonella* bacterium cells. In another embodiment, the cells are isolated from an organism selected from the group consisting of invertebrates, mammals, bacteria and yeast. In yet another embodiment, the cells are freshly isolated. In yet another embodiment, the cells comprise a cell line.

In yet another embodiment of the present invention, the culture is maintained with the nanomaterials for a period of time extending from 1 hour to 4 weeks. In another embodiment, the culture is maintained with the nanomaterials for a period of time extending from 1 hour to 24 hours.

In one embodiment of the present invention, the assay for ROS production comprises measuring the levels of reduced and oxidized glutathione of the cells. In another embodiment, the assay for ROS production comprises detecting the presence of superoxide or $H_2O_2$ radicals in the cells, as well as in the tissue culture medium. In yet another embodiment, the assay for ROS production further comprises measuring the levels of reduced and oxidized glutathione in the cells and detecting the presence of superoxide or $H_2O_2$ radicals in the cells.

In another embodiment of the present invention, the phase II antioxidant molecule or enzyme is at least one molecule selected from the group consisting of heme oxygenase 1 (HO-1), catalase, superoxide dismutase, glutathione-S-transferase (all isozymes), glutathione peroxidase, glutathione reductase, and thioredoxin reductase. In another embodiment, the assay for phase II antioxidant molecule expression comprises measuring the levels of antioxidant proteins in the cells. In yet another embodiment, the assay for phase II antioxidant molecule expression comprises measuring the mRNA levels of antioxidant proteins in the cells. In another embodiment, the assay for phase II antioxidant molecule expression comprises measuring the levels of antioxidant proteins in the cells and measuring the mRNA levels of the antioxidant proteins in the cells.

In another embodiment of the present invention, the proinflammatory cascade comprises MAP kinase and NF-kappa B cascades. In another embodiment, the MAP kinases are selected from the group consisting of Jun kinase, ERK and p38 MAP kinase. In another embodiment, the NF-kappa B cascade comprises the I kappa B kinases, the I kappa B protein, and the NF-kappa B transcription factors.

In another embodiment of the present invention, the assays for activation of the proinflammatory cascades comprise measuring the phosphorylation status of MAP kinases in the cells. In another embodiment, the assays for the activation of the proinflammatory cascades comprises measuring activation of pro-inflammatory molecules selected from the group consisting of cytokines, chemokines and adhesion molecules in the cells. In another embodiment, the cytokines, chemokines and adhesion molecules are selected from the group consisting of IL-8, IL-6, TNF-α, MCP-1, M-CSF, GM-CSF, RANTES, eotaxin, ICAM-1, VCAM-1 and other related MAP kinase-dependant pro-inflammatory products.

In one embodiment of the present invention, the method further comprises introducing a quantity of the NM into a subject and performing on the subject assays for oxidative stress. In another embodiment, the subject is selected from the group consisting of invertebrates, yeast, bacteria, dogs, cats, rodents, pigs, non-human primates and humans. In yet another embodiment, the test subject is a transgenic animal.

BRIEF DESCRIPTION OF THE FIGURES

The accompanying figures illustrate several embodiments of the present invention and, together with the description, service to explain the principles of the invention. However, the figures are not required to understand the invention. These figures, as well as the following detailed description and the examples, are only for the purpose of illustrating a preferred embodiment of the invention and are not to be construed as limiting the invention.

FIG. 4D depicts the chemical composition of UFP and the content of transition metals and polycyclic aromatic hydrocarbons (PAHs). Abbreviations: BAA, benzo(a)anthracene; BAP, benzo(a)pyrene; BBF, benzo(b)fluoranthene; BGP, benzo(ghi)perylene; BKF, benzo(k)fluoranthene; CRY, chrysene; FLT, fluoranthene; IND, indeno(1,2,3-cd)pyrene; PHE, phenanthrene; PYR, pyrene. LOD=limit of detection.

FIG. 17A-F depicts electron micrographs of the uptake and subcellular localization of NP according to the teachings of the present invention. (A) Untreated RAW 264.7 cells; (B) cells treated with UFP; (C) cells treated with $TiO_2$, (D) cells treated with fullerol, (E) cells treated with COOH-PS nanospheres, (F) cells treated with $NH_2$-PS. Labels: M=mitochondria, P=particles.

DETAILED DESCRIPTION OF THE INVENTION

Figure 1:
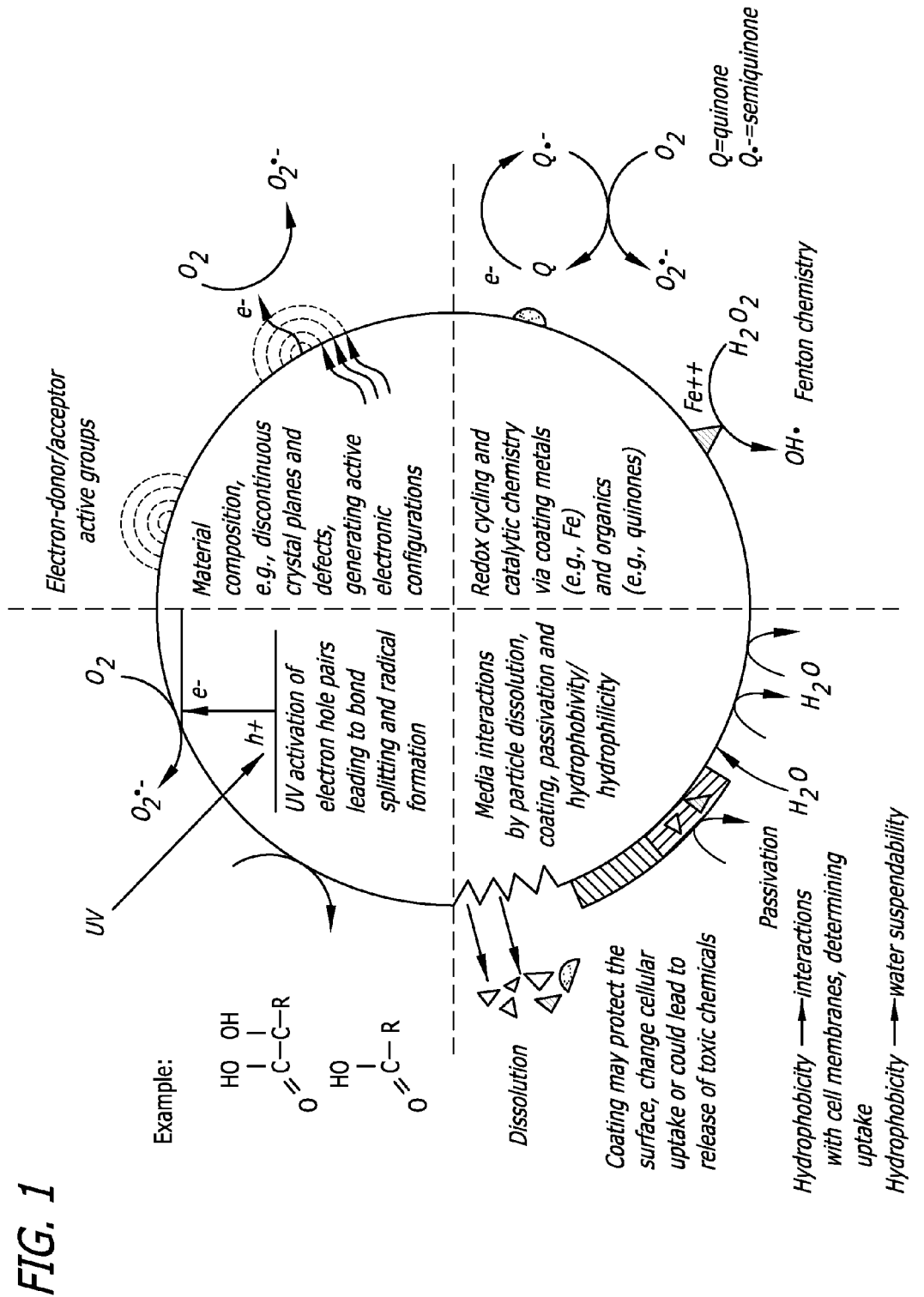
FIG. 1 schematically depicts the oxidative stress to redox cycling diesel exhaust particles.

The present invention provides methods to assess the potential adverse biological effects of engineered nanomaterials (NM) as well as ambient ultrafine particles from emission sources. Specifically, the generation of reactive oxygen species (ROS) and oxidative injury provides means for quantitative measures of nanomaterial toxicological effects. As used herein, the term "nanomaterials" refers to materials with structural features (particle size or grain size, for example) of at least one dimension in the range 1-100 nm. Exemplary nanomaterials include, but are not limited to engineered nanoparticles, ambient ultrafine particles, nanotubes, nanofibers, nanocrystals, fullerenes, dendrimers, block copolymers, nanofilms and nanocomposites.

Furthermore, the methods of the present invention can be used to assess the potential adverse biological effects of incidental ambient nanoparticles. The latter particle type includes diesel exhaust and fossil fuel combustion particles that are initially shed as "ultrafine"_particles in the ambient air.

Prior to this invention, there have been scattered and descriptive attempts to study the toxicity of engineered NM. From the limited research data that became available, there is evidence suggesting that engineered NM generate adverse biological effects through the generation of reactive oxygen species (ROS) as well as other biological pathways. Biological systems integrate multiple pathways of injury into a limited number of pathological outcomes, including inflammation, cytotoxicity, apoptosis, necrosis, fibrosis, hypertrophy, metaplasia and carcinogenesis (Table 1). Although oxidative stress is involved in most of these outcomes, other mechanisms of injury are also possible. These other mechanisms, include, but are not limited to, disruption of biological membranes, protein denaturation, DNA damage, immune reactivity and the formation of foreign body granuloma.

TABLE 1

| Pathophysiological effects of nanomaterials | |
|---|---|
| Experimental effects of nanomaterials | Potential pathophysiological outcomes |
| ROS generation | Protein, DNA and membrane injury, oxidative stress |
| Oxidative stress | Phase II enzyme induction, inflammation, mitochondrial perturbation. |

TABLE 1-continued

Pathophysiological effects of nanomaterials

| Experimental effects of nanomaterials | Potential pathophysiological outcomes |
|---|---|
| Mitochondrial perturbation | Inner membrane damage, PTP opening, energy failure, apoptosis, apo-necrosis, cytotoxicity |
| Inflammation | Tissue infiltration with inflammatory cells, fibrosis, granulomas, atherogenesis, actute phase protein expression (e.g., C-reactive protein) |
| Uptake by reticulo-endothelial system | Asymptomatic sequestration and storage in liver, spleen, lymph nodes, possible organ enlargement and dysfunction. |
| Protein denaturation, degradation | Loss of enzyme activity, auto-antigenicity |
| Nuclear uptake | DNA damage, nucleoprotein clumping, autoantigens |
| Uptake in neuronal tissue | Brain and peripheral nervous system injury |
| Perturbation of phagocytic function, particle overload, mediator release | Chronic inflammation, fibrosis, granulomas, interference in clearance of infectious agents |
| Endothelial dysfunction, effects on blood clotting | Atherogenesis, thrombosis, stroke, myocardial infaction. |
| Generation of neo-antigens, breakdown in immune tolerance | Autoimmunity, adjuvant effects |
| Altered cell cycle regulation | Proliferation, cull cycle arrest, senescence |
| DNA damage | Mutagenesis, metaplasia, carcinogenesis |

The decrease in size and increase in surface area of a NM often result in altered physicochemical and surface structural properties of the NM. These include placement of more electron-donor/acceptor active sites that can participate in interactions with molecular dioxygen ($O_2$) on the particle surface. The $O_2$ is capable of capturing some of the stored electrons when it binds to the particle surface in the vicinity of the active sites. One electron reduction of $O_2$ generates the superoxide radical ($O_2.^-$), which could lead to the production of $H_2O_2$ and additional reactive oxygen species (ROS). Under normal coupling conditions, ROS are generated at low frequency and are easily neutralized by antioxidant defenses such as glutathione (GSH) and antioxidant enzymes. However, under conditions of excessive ROS production, ROS deplete cellular GSH, which leads to an increase in glutathione disulfide (GSSG). A decrease in the GSH/GSSG ratio disturbs the redox equilibrium and leads to a state of oxidative stress in the target tissue. Oxidative stress is a biological emergency that can trigger inflammation and other toxic effects. In addition to the generation of pro-inflammatory effects, nanomaterials of various sizes and chemical composition are able to lodge in mitochondria. This can lead to disruption of the mitochondrial electron transduction chain, which leads to additional $O_2.^-$ production. This can also perturb the mitochondrial permeability transition pore, which leads to the release of pro-apoptotic factors and programmed cell death. FIG. 1 illustrates the effects of nanomaterial composition, electronic structure, bonded surface species (e.g. metal containing), surface coatings (active, passive) and solubility including the contribution of surface species and coatings and interactions with other environmental factors (e.g., UV activation).

Figure 2:
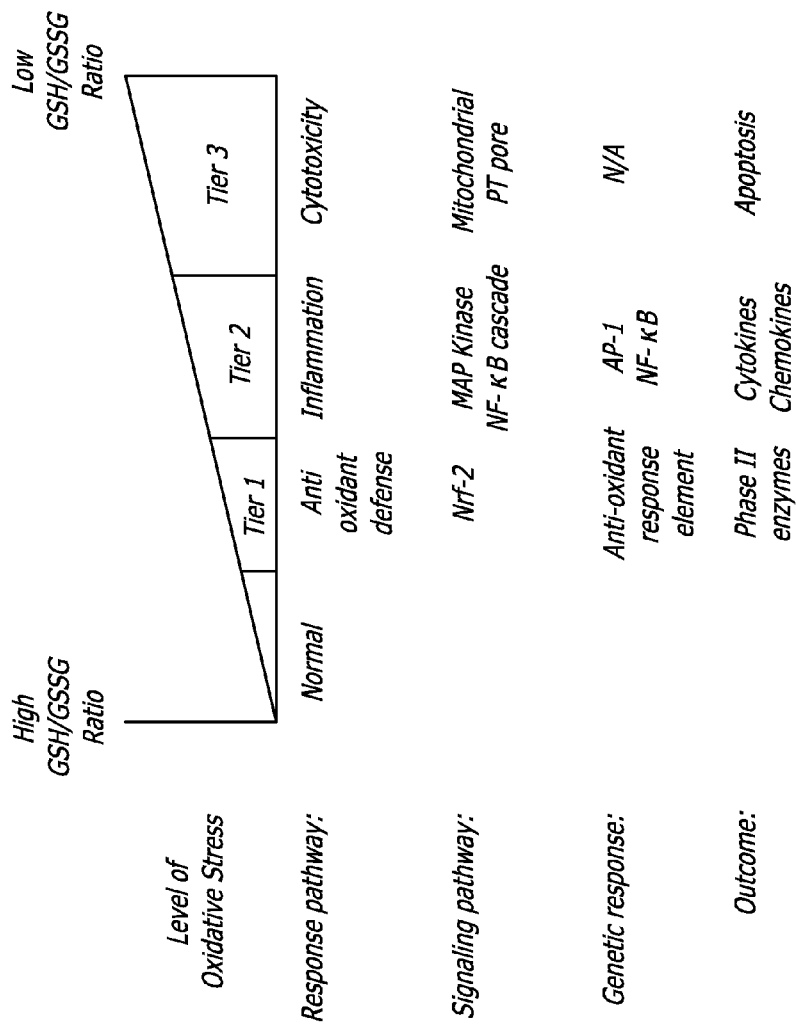
FIG. 2 schematically depicts the interaction mechanisms of nanomaterials in biological tissues.
Figures 3A, 3B:
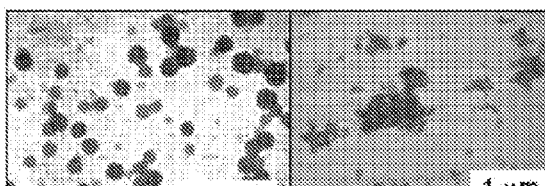
FIG. 3A-H depicts transmission electron micrographs of nanoparticles (NP). (A) Polystyrene nanospheres (PS, 60 nm); (B) carbon black; (C) carboxylated polystyrene nanospheres (COOH-PS, 60 nm); (D) $TiO_2$; (E) amino polystyrene nanospheres ($NH_2$-PS, 60 nm); (F) fullerol; (G) $NH_2$-PS (600 nm); and (H) ultrafine particles.
Figures 3C, 3D:
Figures 3E, 3F:
Figures 3G, 3H:
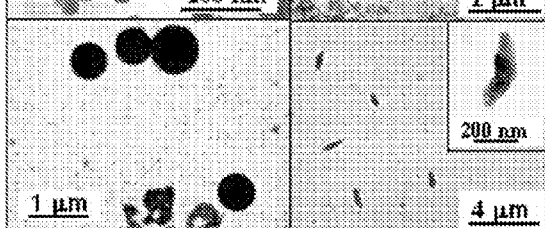

Reactive oxygen species do not automatically induce injury unless the production of ROS is sufficiently high to break through a protective barrier to cause injury. Thus, there is a protective mechanism that is turned on by ROS that functions by a negative feedback mechanism to switch off ROS production. This defense needs to be overwhelmed before a subject exposed to ambient particulate matter develops injury. When this barrier is exceeded and tissue injury sets in, it also follows a logical series of steps that involves specific cellular and genetic activation pathways (FIG. 2).

The present invention provides a novel, predictive scientific approach and protocols to study the potential toxicity of engineered NM. The methods of determining the toxicity of nanomaterials in the present invention can be illustrated by the following series of events: protective cellular responses (Tier 1) leads to pro-inflammatory responses (Tier 2) which in turn cause tissue damaging or cytotoxic responses (Tier 3). At the lowest level of oxidative stress, cells and tissues respond by activating genes that encode for a number of phase II antioxidant and detoxification enzymes. Phase II antioxidant molecules or enzymes are selected from more than 200 related products including, but not limited to, heme oxygenase 1 (HO-1), catalase, superoxide dismutase, glutathione-S-transferase (all isozymes), glutathione peroxidase, glutathione reductase, NADPH quinine oxidoreductase, UDP-glucoronosyltransferase and thioredoxin reductase. These enzymes function by neutralizing ROS and terminating the particle-induced chemistry that is involved in ROS production. A reduced or compromised phase II response promotes susceptibility to oxidant injury. This tier of oxidative stress, Tier 1, is often successful in preventing adverse tissue effects and disease. Tier 1 responses can be studied using genetic and protein chemistry tools that reflect the expression of the phase II antioxidant and detoxification enzymes. These assays are available to assess NM effects on tissue culture cells as well as animal models that are dependent on the generation of oxidative stress to promote heart and lung and possibly other disease. The sensitivity of Tier 1 responses makes them good biomarkers for reporting the generation of oxidative stress in cell cultures and biological tissue that come into contact with NM. Because Tier 1 responses are protective in nature, their induction does not automatically signify disease development, but nonetheless provides early warning signals that some oxidative stress is being induced, and that this could be on a trajectory to more dangerous effects, which are the biological outcome of Tiers 2 and 3 responses.

Tier 2 represents tissue injury through the generation of inflammation as well as other pathological manifestations. Testing for the pro-inflammatory proteins and gene products as well as signaling pathways that characterizes Tier 2 provides a predictive model of toxicity by which the basic toxicological manifestations at the NM and cellular level can be extrapolated to a disease process in live animals and humans.

Tools have been developed to define the pro-inflammatory products of Tier 2, both at the gene and protein levels and these assays can be used to study NM toxicity at the cellular level. This includes the detection of cytokines, chemokines, adhesion molecules and other inflammatory products that reflect local and systemic inflammatory responses. Oxidative stress and ROS turn on pro-inflammatory cascades through mechanistic pathways, including cellular activation cascades (also known as signal transduction pathways), which can be followed by biochemical and imaging methods.

Tier 3 represents toxicity that culminates in mitochondrial damage and programmed cell death. In assessing the direct effect of engineered NM on cells, mitochondrial perturbation, calcium flux, programmed cell death or cytotoxic responses are useful screening assays that can be used as a direct test of material toxicity. Moreover, the mechanism by which engineered NM lead to cell death in some instances is dependent on the particle entrance into the cell and targeting of mitochondria. The mitochondrion is the fuel source of the cell and is essential for maintenance of cellular function. In addition to ambient nanoparticles, it has also been shown that several other types of ambient nanoparticles and engineered NM can gain access to mitochondria, with the possibility of initiating cytotoxic responses.

Predictive in vitro screening assays based on an understanding of the mechanism of injury are generally regarded as the preferable toxicity screen because the outcome is anchored to an in vivo outcome in a live animal or humans. These outcomes include toxic responses to chemicals and nanoparticle exposures. The test principles disclosed herein, namely generation of oxygen radicals and oxidative stress, has been linked to heart and lung and possibly other disease in animals and humans exposed to pollutant particles in the air and is the best developed toxicological mechanism by which ambient nanoparticles and a small number of NM have been shown to induce tissue injury. This may be related to the exposure means and portal of entry of the particles into the organism. Therefore the principle of oxidative stress is also applicable to injury outside of the lung, including the cardiovascular system, skin, brain, peripheral nervous system, immune system, liver, spleen, kidney, endocrine system and other systemic responses. Organ systems and a possible range of cellular toxic responses in those organs are depicted in Table 2. Using cellular assays in which NM are tested for oxidative injury to cells, representative of a number of body organs and tissues, is the most cost effective way to screen for nanotoxicity. Examples of the cell types that are representative of the range of tissues and impacted organs include macrophages, epithelial cells, endothelial cells, keratinocytes, neuronal cells, kidney cell, liver cells and antigen-presenting cells. In addition, the *Salmonella* bacterium can be used for scanning of mutagenicity in the Ames test. Suitable cells can be obtained from vertebrate or invertebrate organisms including, but not limited to, mammals, bacteria, and yeast. Mammals include, but are not limited to humans, non-human primates, rodents, dogs, cats, cattle and pigs.

TABLE 2

In vitro systems defined by portal of entry and potential target organs

| Portal of entry | Cell/Tissue Type | Cellular response/pathology |
|---|---|---|
| Lung | Epithelium | Toxicity, inflammation, translocation, carcinogenesis |
|  | Macrophages | Toxicity, chemotaxis, phagocytosis, inflammation |
| Skin | Keratinocytes | Cytotoxicity, inflammation |
| Mucosa | Buccal/intestinal epithelium | Cytotoxicity, inflammation, translocation |
| Cardiovascular system | Endothelial cells (e.g. vascular endothelial cells) | Cytotoxicity, homeostasis, translocation |
| Blood | Red blood cells, platelets, bone marrow (megakaryocytes) | Inflammation, immune responses |
| Liver | Hepatocytes | Toxicity |
|  | Kupffer cells | Inflammation, coagulation |
| Spleen | Lymphocytes | Immune response |
| Central and peripheral nervous system | Neuronal cells | Toxicity, inflammation, translocation |
|  | Astroglia, microglia | Inflammation |
| Heart | Cardiomyocytes | Toxicity, inflammation, fuction |
| Kidney | Multiple cell types | Toxicity, inflammation, translocation |

Although the elucidation of a cellular response does not automatically signify in vivo toxicity, a lack of responsiveness at this level predicts that the material is likely to be inert from oxidative stress injury in vivo. Predictive in vitro testing also allows high throughput screening and reduces the need to perform large-scale and expensive animal experiments for every assessment. This is an important consideration for nanotechnology in light of the sobering statistic that among the 80,000 chemicals that are registered for commercial use in the US, the National Toxicology Program has only assessed approximately 530 chemicals long-term and approximately 70 chemicals short-term in toxicity studies since 1978. It is possible that the field of nanotechnology may be faced with similar numbers of new materials.

In one embodiment, the present invention provides an in vitro test strategy to assess ROS production and the different tiers of oxidative stress in cells by assessing cellular stimulation, ROS and cellular glutathione content, cellular uptake and subcellular localization of nanoparticles and Tier 1, Tier 2 and Tier 3 oxidative stress responses.

Cellular stimulation is measured by exposing cells to a log-dose range of particles for a period of time from several minutes to weeks or months. Stable polar particles may require mechanical dispersion while nonpolar particles, which have the tendency to aggregate, may require the use of surface active treatments and chemical modification to disperse these particles.

Reactive oxygen species and cellular glutathione content are measured after incubation with incremental amounts of stimuli. In one embodiment, reduced and oxidized glutathione content is measured by the method of Tietze (Anal Biochem 27:502, 1969). In another embodiment, intracellular reduced thiol levels can be determined by a flow cytometry procedure that utilizes the fluorescent dye, monobromobimane. ROS production is determined by flow cytometry methods to detect the production of superoxide and $H_2O_2$ radicals. Hydrogen peroxide generation can additionally be measured by dichlorofluorescein acetate (DCF) fluorescence, and the superoxide radical determined by hydroethidium and MitoSOX Red™ fluorescence. Alternatively, ROS production can also be determined by biochemical and enzymatic methods.

Exemplary assays to measure Tier 1, Tier 2 and Tier 3 responses are described in detail below and in Table 3.

TABLE 3

Assays to test reactive oxygen species generation by nanomaterials

|  | Tier 1 Cell and anti-oxidant defense | Tier 2 Inflammation | Tier 3 Cytotoxicity, mitochondrial effects and apopotosis |
|---|---|---|---|
| In vitro | HO-1 WB Phase II mRNA (real time PCR) | Cytokine ELISA Chemokine ELISA Phospho-JNK WB Nf-2 WB Cytokine/chemokine mRNA | Mitochondrial $\Delta\Psi m$ ($DiOC_6$) [Ca2+[i: Fluo-3 [Ca2+]m: Rhod-2 Caspase-3 activation DNA fragmentation (BrdU) |
| In vivo | HO-1 Luc mice | BAL cytokines Inflammatory cells Histology | Cell damage (LDH) Immunohistochemistry (active caspase-3) |

WB = Western blotting; ELISA = enzyme-linked immunosorbent assay;

Tier 1 oxidative stress responses are determined by assessment of phase II antioxidant molecule expression at the protein and the mRNA level. Protein expression can be determined by a variety of methods known to persons of ordinary skill in the art including, but not limited to colorometric assays and immunoblotting, while mRNA expression can be determined by methods including, but not limited to, polymerase chain reaction (PCR), quantitative PCR and real-time PCR. Furthermore, reporter gene activity that reflects structural activation of the antioxidant response element (ARE) can be assessed. This genetic response element is responsible for transcriptional activation of more than 200 phase II gene promoters in response to the transcription factor Nrf2. In one embodiment, ARE reporter gene activity is assessed by using a RAW 264.7 cell line (mouse leukemic monocyte macrophage cell line), which has been stably transfected with a triplicate repeat of the ARE linked to a luciferase reporter. This cell line can be used as a high throughput screen to handle multiple samples simultaneously.

Tier 2 oxidative stress responses are determined by assessment of MAP kinase and NF-kappa B signaling cascades, which are induced at more advanced levels of oxidative stress. These cascades play a role in the induction of several pro-inflammatory cytokines, chemokines and adhesion molecules. Activation of the MAP kinase cascades, including the Jun kinase, p38 MAP kinase and ERK cascades, is studied by an immunoblotting approach that assesses the phosphorylation (activation) status and kinase abundance by a combination of phosphopeptide and protein antibodies. It is also possible to make use of anti-phosphopeptide antibodies for developing flow cytometry procedures. Activation of the NF-kappa B signaling cascade is studied by performing I kappa B kinase assays, determining I kappa B protein degradation by immunoblotting, and determining nuclear release of NF-kappa B transcription factors in electrophoretic mobility shift assays. Quantitative ELISA assays for pro-inflammatory cytokines and chemokines involved in lung and heart disease (e.g. interleukin [IL]-8, IL-6, tumor necrosis factor alpha [TNF-α], monocytes chemoattractant protein 1 [MCP-1], macrophage colony stimulating factor [M-CSF], and interferon-inducible protein 10 [IP-10]), have been established, and can also be combined in a high throughput Multiplex screening procedure that measures several cytokine levels simultaneously. The same analysis can also be conducted by real-time PCR to assess the mRNA expression of a range of cytokines and chemokines. Adhesion molecule expression can be studied by methods including, but not limited to, flow cytometry and fluorescent cell surface staining, immunoblotting or real-time PCR analysis.

Tier 3 oxidative stress responses are determined by assessment of mitochondrial function at the cellular level as well as in isolated mitochondrial preparations. In one embodiment, a cellular assay for mitochondrial perturbation and apoptosis uses established flow cytometric procedures for dual-color annexin V/PI (apoptosis) and dual-color $DiOC_6$/hydroethidine staining (mitochondrial membrane potential and superoxide generation). The effect of engineered NM on isolated liver mitochondria can also be determined in a fiber-optic spectrofluorometer. This instrument performs multi-channel display of mitochondrial volume/swelling, TMRM uptake, Calcium Green-5N fluorescence and oxygen consumption, thereby reflecting PT pore opening, mitochondrial membrane potential, mitochondrial $Ca^{2+}$ retention capacity and respiration, respectively.

In another non-limiting example, cellular uptake and subcellular localization of nanoparticles, e.g., targeting of mitochondria, will be studied by electron microscopy and confocal microscopy.

The in vitro assays described can be used selectively for individual nanomaterials. For instance, if initial testing does not show ROS production or a depletion of the cellular glutathione content, it may be necessary to select only a few of the more sensitive assays for each Tier of oxidative stress. As different types of NM are being introduced, decision matrixes are developed to test each type of product as would be understood by persons of ordinary skill in the art.

In one embodiment, if NM have been shown to induce ROS production during nanoparticle testing and oxidative stress during in vitro biological testing, in vivo toxicity testing can be conducted. Animals or organisms suitable for this in vivo toxicity testing include, but are not limited to, invertebrates, yeast, bacteria, dogs, cats, rodents, pigs, non-human primates and humans. Furthermore, the test subjects can include transgenic animals that have been genetically engineered to provide a rapid readout of oxidative stress. In addition, where such evidence is obtained, it is possible to conduct testing in animal disease models where oxidative stress plays a role in disease pathogenesis including, but not limited to, asthma, atherosclerosis, diabetes mellitus, auto-immunity, and neurological disease.

As with in vitro assays, the appropriate in vivo assay is selected by the type of NM and the method of exposure. In a non-limiting example, for particle exposure to the lungs, assays that elucidate the effects of exposure of the particles to the lungs via inhalation or intratracheal instillation may be warranted.

Furthermore, a number of animal models allow the study of mechanistic pathways by live imaging procedures. One non-limiting example is the use of a transgenic mouse model in which the HO-1 promoter has been linked to a luciferase reporter (Contag C H and Stevenson D K, J Perinatol 21 Supplement:S119-S124, 2001, which is incorporated by reference herein for all it contains regarding HO-1 transcription). The ROS-generating ability of ambient UFP has been assessed in this model. Similar imaging models exist to study the activation of the NF-kappa B signaling cascade.

The adverse biological effects of ambient ultrafine particles have been assessed in the methods of the present invention along with representative manufactured nanoparticles (see also Xia T, et al. Nano Lett 6:1794-807, 2006, which is incorporated by reference herein for all it contains regarding toxicity studies on nanoparticles). Studies were carried out in an exemplary phagocytic cell line (RAW 264.7) that is representative of the macrophages and dendritic cells that are targeted by aerosolized nanoparticles in the lung. Characterization of the physicochemical properties a series of NP (ultrafine particles (UFP), titanium dioxide, carbon black (CB), fullerol and polystyrene (PS) nanoparticles) shows a dramatic change in their state of aggregation, dispersibility and charge during transfer from an aqueous solution to protein-containing tissue culture medium. Nanoparticles also differ with respect to cellular uptake, subcellular localization and ability to catalyze ROS production under biotic and abiotic conditions. Ambient UFPs and cationic PS nanospheres were capable of ROS production, thiol depletion and the induction of mitochondrial damage and cellular toxicity.

The unique physicochemical properties of nanoparticles are attributable to variables such as a small size, large surface area, chemical composition, crystallinity, electronic properties, surface reactivity, inorganic/organic coatings, solubility, shape and state of aggregation. Particles less than 100 nm in size fall in the transitional zone between individual molecules and bulk materials of the same composition. As the particle diameter approaches the nanoscale dimension, there is a dramatic increase in its surface area and display of chemically reactive molecules on its surface that could play a role in the adverse biological effects. For instance, a change in the material properties to create discontinuous crystal planes or enhance electron storage can contribute to ROS generation. Alternatively, the increased surface reactivity can lead to protein denaturation, membrane damage, DNA cleavage, immune reactivity and inflammation. The small size of CP is also responsible for deep penetration in the lung where they have a high rate of retention due to van der Waals interactions. Ultimately the effect of the small particle size combines with particle number and surface area to determine the actual dose of exposure.

Previous studies on the toxicological effects of diesel exhaust particles (DEP), which are emitted in the nano-range, demonstrated their ability to induce ROS, oxidative stress and mitochondrial damage in target cells such as alveolar macrophages and bronchial epithelial cells. Cellular studies have also demonstrated that organic DEP extracts induce protective and injurious cellular responses, including the expression of phase II enzymes, cytokine and chemokine production, and the initiation of programmed cell death. These constitute the elements of the hierarchical oxidative stress response. Ultrafine particles induce similar effects as DEP. Protective and injurious cellular responses are in dynamic equilibrium, and weakening or strengthening of the phase II response determines susceptibility to oxidant injury. This principle is illustrated by the use of sulforaphane (SFN), a nontoxic chemical that induces a phase II response in RAW 264.7 cells and subsequent SFN administration protects these cells from pro-inflammatory and cytotoxic effects.

Redox-cycling organic chemicals and transition metals also play an important role in particle-induced ROS generation including $H_2O_2$ production, which most likely originates from $O_2.^-$ through spontaneous or enzyme-catalyzed dismutation. Functionalized organic chemical groups, such as oxy-PAH and quinones, are capable of $O_2.^-$ generation by redox cycling reactions that involve the formation of a metastable intermediary electron acceptor (e.g. semiquinones). Enzyme-assisted one-electron transfers, e.g., microsomal NADPH-P450 reductase, can strengthen this reaction in cells. The presence of transition metals assists in the formation of additional radical species, e.g., the hydroxyl radical (OH.), through the catalysis of the Fenton reaction. Mitochondrial perturbation represents yet another source of UFP-induced ROS generation involving interference in inner membrane electron transfer, mitochondrial depolarization and opening of the PTP in response to PM chemicals. Hydrogen peroxide generation by UFP commences early and then declines by 4 hrs, while $O_2.^-$-production starts later and is progressive in nature. These different phases of ROS production represent different mechanisms. The early phase of ROS production may be due to redox cycling chemistry, while mitochondria are responsible for the late and progressive increase in $O_2.^-$. In contrast to ambient UFP, CB particles contains small quantities of redox cycling chemicals and are incapable of ROS generation.

ROS generation by $TiO_2$ occurs when absorbed photons promote electrons across the $TiO_2$ band gap to the conduction band, simultaneously creating a vacancy or hole in the valence band of the semiconductor. Electrons that diffuse to the surface may react with oxygen to form the $O_2.^-$. Electron holes that diffuse to the surface may react with adsorbed water to form hydroxyl radicals. $TiO_2$ does not form these highly reactive species in the dark. The rutile form of $TiO_2$ absorbs light over a slightly broader range of wavelengths than does the anatase form. However, it is the anatase form that exhibits a higher photocatalytic activity.

ROS production by fullerol occurs via two pathways. In the first, a photon can excite fullerol from the ground to a singlet state, where it has a nanosecond lifetime. Singlet state fullerol may then relax to the longer-lived triplet state where it readily reacts with ground-state oxygen to form singlet oxygen via what is known as a type I pathway. The triplet state fullerol can also be reduced by appropriate electron donors and subsequently oxidized by oxygen to form $O_2.^-$ via the type II pathway. Alternatively, in the absence of light and in the appropriate redox conditions, fullerol may act as an electron shuttle between electron donors and oxygen to form $O_2.^-$. Fullerol induces spontaneous as well as cellular ROS production.

Although capable of ROS generation and cellular toxicity, cationic PS nanospheres differ in their action from ambient UFP. This includes lack of spontaneous ROS generation, different kinetics of the cellular ROS response, and a failure to induce TNF-α production. It has been suggested that some of the effects of positively-charged polyamine-coated PS microparticles are due to strong ionic interactions with the negatively-charged cell membrane. The strength of these interactions facilitates particle uptake into tight-fitting phagosomes, compared to the more loose-fitting phagosomes that forms around negatively-charged particles. Tight adherence of the cationic particles to the membrane interferes in phagosomal fusion with lysosomes. As a result, these phagosomes become isolated in the cytoplasm, with the possibility that the particles could escape to the cytosol after endosomal rupture. Behr proposed the so-called proton sponge hypothesis to explain the mechanism of rupture (Boussif O, et al., Proc Natl Acad Sci USA 92:7297-301, 1995). His theory posits that extensive buffering by the cationic particle surface may lead to unchecked proton transport into the phagosome. This could lead to excessive water influx, which due to the space constraints, leads to endosome rupture. From there, the particles may engage other membrane-protected spaces, such as mitochondria. The above sequence of events may explain the formation of particle-filled vacuoles and the disappearance of mitochondria from the cell. Mitochondrial destruction may be instrumental in the late phase of $O_2.^-$ production. Although it is uncertain what the origin is of the first wave of ROS production, it is possible that $NH_2$-PS could induce the assembly and activation of NADPH oxidase; this enzyme is responsible for $O_2.^-$ production in the phagosomal membrane. While the first wave of $O_2.^-$ generation is insensitive to NAC quenching, this antioxidant could suppress the second wave of $NH_2$-PS-induced $O_2.^-$ generation. NAC is capable of suppressing $O_2.^-$ production in mitochondria from cells undergoing apoptosis.

The present invention provides the methods and systems to distinguish potentially toxic from nontoxic particles and to interpret the range of cellular responses in terms of the hierarchical oxidative stress paradigm, which includes both protective and injurious effects. Therefore ROS generation and oxidative stress can be used as a paradigm to assess NP toxicity. Although not all NP exhibit the electronic configurations or surface properties that allow spontaneous ROS generation, particle interactions with cellular components can cause ROS generation as a result of such perturbation. The magnitude of ROS production overwhelms the antioxidant defense of the cell or induce mitochondrial apoptotic mechanisms and cellular toxicity results.

EXAMPLES

Example 1

Particle Selection and Physico-Chemical Characterization

Ambient UFP (<0.15 μm) were collected in the Los Angeles basin using the Versatile Aerosol Concentration Enrichment System (VACES) (Li N, et al., Eviron Health Perspect 111:455-60, 2003). The concentration enrichment process does not alter the physical, chemical, and morphologic properties of the particles. The particle concentration in the aqueous medium was calculated by dividing the particle loading by the total volume collected over that time period. The sample was collected at the University of Southern California (USC), which represents a typical urban site. The aerosols at this site are mostly generated from fresh vehicular emissions. The content of 16 signature polycyclic aromatic hydrocarbons (PAHs) in each collection was determined by HPLC-fluorescence. Heavy metal and other components were determined by Inductively Coupled Plasma Mass Spectroscopy (ICP-MS).

All nanoparticles were characterized in terms of size, shape, charge, and relative hydrophobicity (Table 4). Nanoparticle shape and structure was characterized using a transmission electron microscope (JEOL JEM 2010, JEOL USA, Inc., Peabody, Mass.). Microfilms for TEM imaging were made by placing a drop of the respective NP suspension onto a 200 mesh copper TEM grid (Electron Microscopy Sciences, Washington, Pa.) and then drying at room-temperature overnight. No fewer than five images of each sample were collected to ensure that those reported were representative of the sample at large.

TABLE 4

Nanomaterial characterization

| Parameters | Methods |
| --- | --- |
| Size distribution (primary particles) | TEM, SEM, XRD |
| Shape | TEM, SEM |
| Surface Area | BET |
| Composition | Mass spectrometry, spectroscopy (UV, Vis, Raman, IR, NMR) |
| Hydrophobilicy | MATH |
| Surface charge - suspension/solution | Zeta potential |
| Crystal structure | TEM, XRD |
| Agglomeration state | TEM, XRD |
| Porosity | MIP |
| Heterogeneity | TEM, SEM, spectroscopy |
| ROS generation capacity | DTT, FFA assay, nanosensors |

TEM = transmission electron microscopy; SEM = scanning electron microscopy; XRD = X-ray diffraction; BET = Brunauer, Emmett and Teller; MATH = microbial adhesion to hydrocarbons; DLS = dynamic light scattering; MIP = mercury intrusion porosimeter; FFA = furfuryl alcohol; DTT = dithiothreitol; IR = infrared; NMR = nuclear magnetic imaging; UV = ultraviolet.

Particle size distribution (PSD) measurements were carried out using a Malvern Zetasizer Nano ZS (Malvern Instruments, Worcestershire, UK). This instrument is equipped with a helium/neon laser (I=633.4 nm) and measures the backscatter from a suspension at an angle of 173°. It is capable of measuring particles in the size range 0.6 nm-6 mm. Size measurements were performed on dilute NP suspensions in 10 mM NaCl solutions at pH 6. The Zetasizer was also used to measure the electrophoretic mobility of the NP suspended in solutions of 10 mM NaCl. Electrophoretic mobility may be used as an approximation of particle surface charge and can be used to calculate zeta potential. The isoelectric point (IEP) for each of the different NP was determined by measuring the change in electrophoretic mobility as a function of pH in a 10 mM NaCl solution. Solution pH was adjusted using either NaOH or HCl. The Helmholtz-Smoluchowski equation was used to correlate electrophoretic mobility to zeta potential. The PSD and electrophoretic mobility of all NP were also measured in the complete culture media for comparison.

The relative hydrophobicity of the various NP was assessed using a hydrocarbon partitioning test with laboratory-grade n-dodecane (Fisher Scientific, Pittsburgh, Pa.). Samples were prepared by adding 4 ml of NP suspension at a concentration of approximately 5 mg/L to a test tube containing 1 ml of dodecane. The test tube was vortexed for 2 min, followed by a 15 min rest period to allow for phase separation. The relative hydrophobicity was assessed as the fraction of the initial NP concentration that partitioned into the dodecane from the aqueous phase.

The particles and their characteristics are listed in Table 5 and their corresponding TEM images are shown in FIG. 3. Ambient UFP were chosen as a NP source that exhibit known health risks and have a defined mechanism of biological injury, namely, ROS generation. Atmospheric UFP have a mean aerodynamic diameter of 30 nm (FIG. 4), which assumes that these particulates have a spherical shape. However, combustion-generated particles have the tendency to grow from nearly spherical primary particles into fractal-like agglomerates with high carbon content. Diesel engines, in particular, emit large amounts of agglomerate soot particles. To conduct biological experiments, the effluent line of the VACES was connected to a liquid impinger, which allows the supersaturated UFP to be collected as water droplets. When suspended in water, the UFP agglomerates form fractal structures (FIG. 3H).

TABLE 5

Physical characterization of nanoparticles

| Particle | Average Diameter (nm) | PDI | Electrophoretic mobility U ($\mu$m cm/Vs) | Zetal potential $\xi$ (mV) | MATH (%) |
| --- | --- | --- | --- | --- | --- |
| In Aqueous Media | | | | | |
| UFP | 1034 | 1.0 | −2.28 | −29.1 | 8.2 |
| PS | 68 | 0.041 | −2.85 | −36.4 | 2.7 |
| $NH_2$—$PS_{60\,nm}$ | 65 | 0.055 | 3.15 | 40.3 | 5.3 |
| $NH_2$—$PS_{600\,nm}$ | 648 | 0.096 | 3.58 | 45.8 | 4.2 |
| COOH—PS | 56 | 0.063 | −2.15 | −27.6 | 0.0 |
| $TiO_2$ | 364 | 0.466 | −1.28 | −16.4 | 1.6 |
| Carbon Black | 245 | 0.251 | −4.26 | −54.6 | 7.1 |
| Fullerol | 218 | 0.388 | −1.76 | −22.6 | 0.6 |
| In Cell Culture Medium | | | | | |
| UFP | 1778 | 0.379 | −0.86 | −11.0 | — |
| PS | 90 | 0.200 | −1.00 | −12.7 | — |
| $NH_2$—$PS_{60\,nm}$ | 527 | 0.339 | −0.87 | −11.1 | — |
| $NH_2$—$PS_{600\,nm}$ | 1913 | 1.0 | −0.96 | −12.2 | — |
| COOH—PS | 82 | 0.191 | −0.85 | −10.9 | — |
| $TiO_2$ | 175 | 0.877 | −0.97 | −12.4 | — |
| Carbon Black | 154 | 0.278 | −1.06 | −13.5 | — |
| Fullerol | 106 | 0.700 | −0.97 | −12.4 | — |

The Mean Particle Size (average diameter) is calculated on an intensity weighted average; PDI = polydispersity index; MATH = microbial adhesion to carbon test.

Ambient UFP collected in downtown Los Angeles are mostly derived from vehicular sources, are heterogeneous in size and are comprised of a solid core made of either inorganic material (sulfuric acid and transition metals) or soot, surrounded by a layer of adsorbed or condensed semi-volatile organic constituents. UFP generate ROS and oxidative stress based on their content of organic chemicals and transition metals. These reactions could take place on the particle surface or the surrounding aqueous medium after leaching of the chemicals from the particle surface. The complete chemical characterization of these particles is shown in FIG. 4. A noteworthy class of components in the organic fraction is polycyclic aromatic hydrocarbons (PAH) (FIG. 4B), including functionalized derivatives such as quinones. Quinones are capable of superoxide ($O_2.^-$) generation through a redox cycling reaction and can also perturb mitochondrial function as will be described later on. Transition metals on the particle surface can contribute to further ROS generation by the Fenton reaction.

Figure 4C:
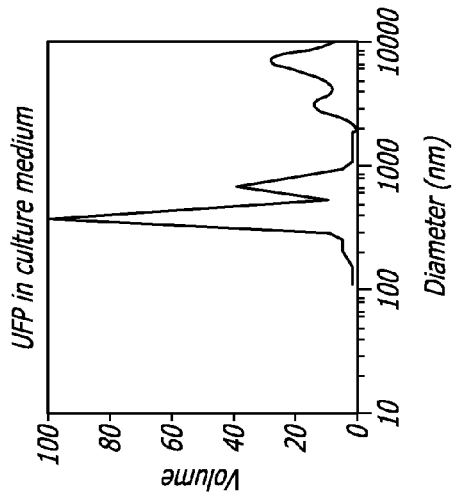
FIG. 4A-D depicts the chemical characterization of NP according to the teachings of the present invention. Size distribution of ambient UFP was measured during aerosolized collection (FIG. 4A) as well as suspended in $H_2O$ (FIG. 4B) and complete culture medium (FIG. 4C).
Figure 4B:
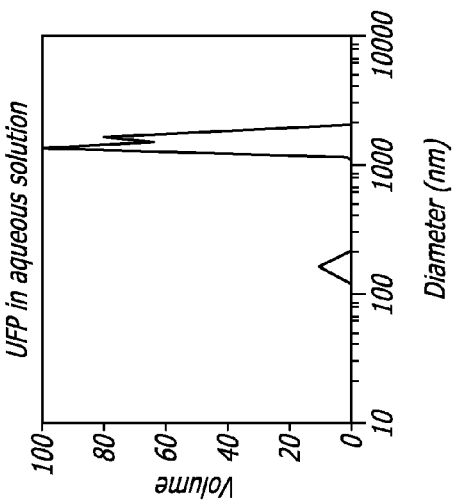
Figure 4A:
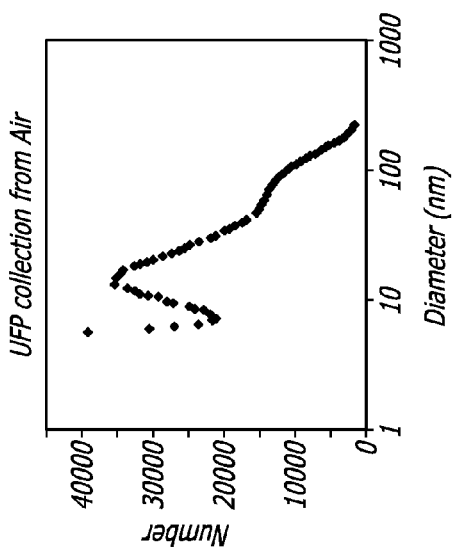
Figure 4D:
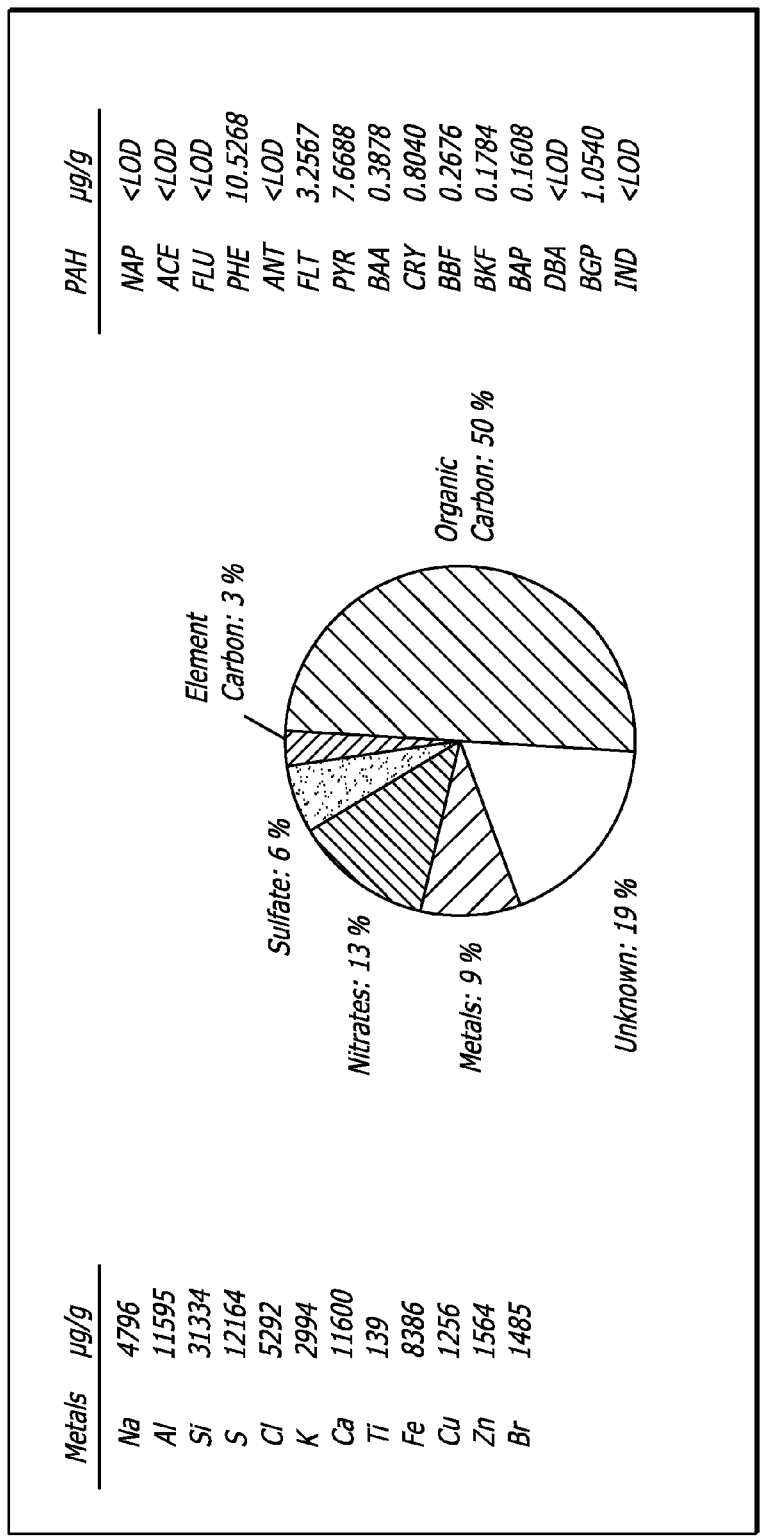

A graphical display of UFP size distribution in aqueous buffer and the culture medium environments is depicted in FIG. 4A. Compared to other particle types, UFP exhibit a high polydispersity index (PDI) (Table 5). These particles are negatively charged in the aqueous buffer as determined by their iso-electrophoretic mobility and zeta potential (Table 5). Due to their coating with organic chemicals, UFP exhibit a relatively high hydrophobicity index, as determined by the microbial adhesion to hydrocarbon (MATH) test (Table 5). The MATH assay assesses NP partitioning between laboratory grade n-dodecane and water. The relatively high hydrophobicity index of these particles could be important for their cellular uptake.

Carbon black (CB) nanoparticles (Printex 90 from Degussa, Hanau, Germany) were included as a control for the UFP. Although these particles have a carbon backbone, they exhibit a low PAH content and no measurable transition metals (Table 6). Since CB nanoparticles are produced in bulk, are in widespread use and could be spread via the air, they are indeed important manufactured NP from a toxicological perspective. These particles have a BET surface area of 300 $m^2/g$ with a mean primary particle diameter of 14 nm. Printex 90 particles exhibit a considerable tendency to aggregate in aqueous medium (FIG. 3B), although not to the same degree as UFP. Their PDI is 0.25, and they exhibit a relatively high hydrophobicity index (Table 5). These particles carry a negative charge.

TABLE 6

Characterization of manufactured NP

|  | CB | $TiO_2$ |
| --- | --- | --- |
| BET | 300 $m^2/g$ | 50 $m^2/g$ |
| Primary particle size | 14 nm | 20-30 nm |
| PAHs (µg/g) | | |
| Phenanthrene | 0.039 | ND |
| Anthracene | 0.001 | ND |
| Fluoranthene | 0.010 | ND |
| Pyrene | 0.065 | ND |
| Benzo(ghi)perylene | 0.008 | ND |
| Benzo(a)pyrene | ND | ND |

PAH contents PAH contents (16 PAHs) were determined by HPLC-FLD after Soxhlet extraction 12 other PAH, including benzo(ghi)perylene that were also measured for UFP (FIG. 4B) were undetectable in CB.
ND, not determined $TiO_2$ is another NP type that is produced in millions of tons per year and is used in a wide range of consumer products and are capable of spontaneous ROS production. The $TiO_2$ NP (P25 particles from Degussa, Hanau, Germany) contain 80% anatase and 20% rutile (Table 6). They have a BET surface area of 50 $m^2/g$, and a primary particle diameter of 20-30 nm. These particles form large aggregates with a PDI of 0.45 (FIG. 3D; Table 5). They carry a negative surface charge and exhibit a relatively low hydrophobicity index.

Fullerol is a hydroxylated $C_{60}$ [$C_{60}(OH)_m$, m=22-26] fullerene derivative that is capable of ROS production under abiotic conditions, but requires an appropriate electron donor to do so. Various forms of fullerenes are emerging as additives to consumer products such as cosmetics, tires, batteries, and tennis rackets. Fullerol forms large aggregates with a PDI of 0.39, a negative zeta potential, and a relatively low hydrophobicity index (FIG. 3F; Table 5).

In contrast with other engineered NP, polystyrene (PS) nanospheres remain monodisperse (PDI<0.1) under aqueous conditions (FIGS. 3A, 3C, 3E and 3G; Table 5). PS particles are available in a variety of sizes as positively charged amino ($NH_2$)-PS or negatively charged carboxylated (COOH)-PS nanospheres. This allows an independent assessment of the role of particle size and charge by a nanomaterial that lacks semiconductor capabilities and is incapable of ROS generation. Physical-chemical analysis reveals that 60 and 600 nm $NH_2$-labeled PS spheres indeed exhibit a positive zeta potential, while that of the 60 nm neutral and COOH-PS nanospheres were negative (Table 5). All PS nanospheres are relatively hydrophobic except for the COOH-PS particles that are more hydrophilic (Table 1).

Figure 5A:
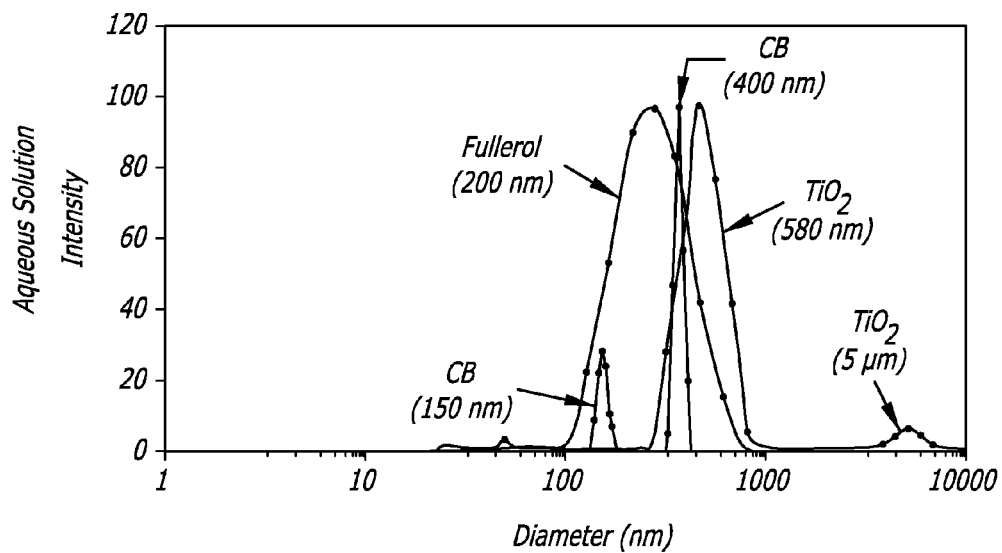
FIG. 5A-B depicts the size distribution of carbon black, $TiO_2$ and fullerol in $H_2O$ (FIG. 5A) and complete culture medium (FIG. 5B) according to the teachings of the present invention.
Figure 5B:
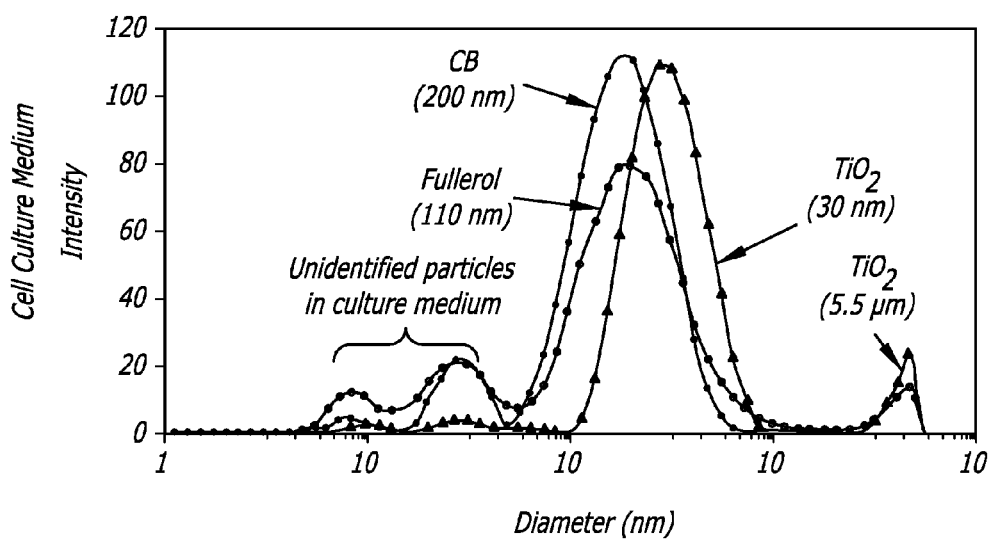
Figure 6A:
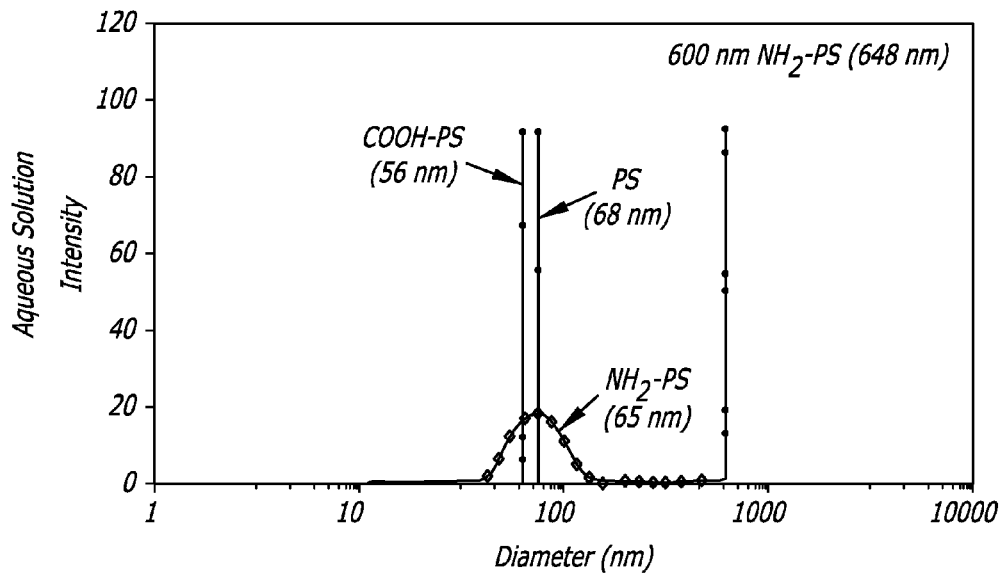
FIG. 6A-B depicts the size distribution of polystyrene particles in $H_2O$ (FIG. 6A) and complete culture medium (FIG. 6B) according to the teachings of the present invention.
Figure 6B:
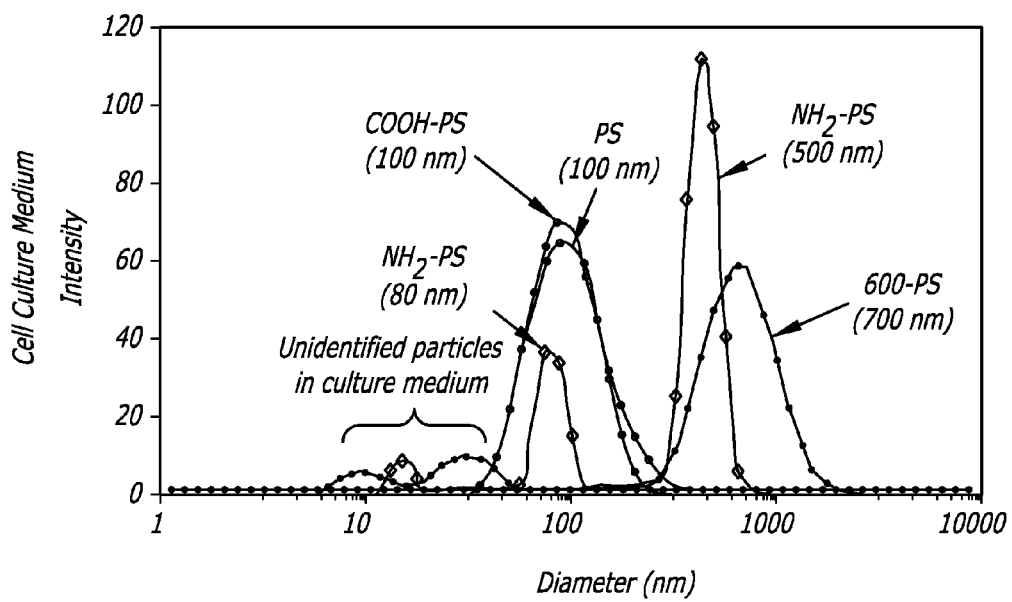

NP characteristics were also assessed in complete culture medium (that includes DMEM and 10% FCS). In the presence of complete medium, $NH_2$-PS particles show a considerable increase in size due to agglomeration, while other NP showed smaller increases or no changes (Table 5, FIGS. 5 and 6). Accordingly, the PDI of $NH_2$-PS particles increased substantially (Table 5). A possible explanation is that proteins in the culture media may be adsorbed onto the particle surface, leading to neutralization of charge and interference in electrostatic repulsion. This notion is supported by the near-equalization of the zeta potential of the particles shown in Table 5 (bottom panel).

Example 2

Assessment of ROS Generation Under Abiotic Conditions

A number of studies indicate that certain NPs exhibit the potential for spontaneous ROS generation based on material composition and surface characteristics. Examples include the presence of redox-cycling chemicals (UFP), crystallinity of the material surface and electronic configurations ($TiO_2$), UV excitability ($TiO_2$ and fullerol), and presence of a conjugated π-bond system (fullerol).

Two complementary techniques were used to assess ROS generation by the NP. The first uses the ROS quencher furfuryl alcohol (FFA) to measure the rate of oxygen consumption as an indirect indicator of the amounts that are being produced. The second assay uses a biosensor to measure $H_2O_2$ production.

Figure 7A:
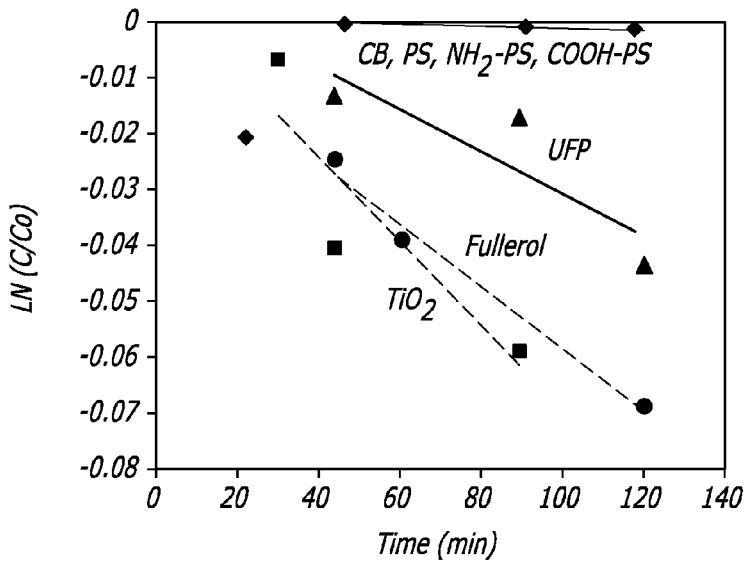
FIG. 7A-B depicts the reactive oxygen species-generating capacity of NP under abiotic conditions according to the teachings of the present invention. (A) furfuryl alcohol (FFA) assay; (B) carbon nanotube-NADH oxidase (CNT-Npx)-bioelectrode cyclic voltammogram.

ROS generation was assessed by the FFA assay of Pickering et al. (*Environ. Sci. Technol.* 39:1359-65, 2005). Four borosilicate glass vials with PTFE-lined caps were filled with a solution consisting of 100 mM fFFA in an aerated phosphate buffer (pH=7). NP were added to a final mass concentration of 0.5 mg/L. Three vials containing the respective nanoparticle solutions were exposed to UV light. A fourth vial served as a non-UV exposed control sample in which all other conditions were maintained similar to the test vials. To ensure that the samples were kept under the same conditions, especially temperature, the control was kept with the irradiated vials. Oxygen consumption was calculated as the difference in dissolved oxygen concentration of the control vial and the average of the three exposed vials. The FFA assay was conducted by suspending the particles in a buffered (pH 7) FFA solution. Identical samples were kept in contact with the NP in UV light and in dark conditions, and compared to blanks containing FFA and buffer without NP. The UV light source had an output spectrum ranging from 310-400 nm, a peak at 365 nm and a total irradiance of 24.1 $W/m^2$. Because FFA quenches ROS production, the quantity of ROS produced is measured as a decrease in dissolved oxygen, corrected for the appropriate blank. This indirect method for measuring ROS has been validated using electron paramagnetic resonance measurements. Results from the indirect measurements are plotted as the log of the ratio of the instantaneous to initial concentrations of oxygen measured over time (FIG. 7). A steeper slope corresponds to a higher rate of ROS production. The $TiO_2$ nanoparticles displayed the highest rate of ROS production under UV irradiation, followed closely by fullerol. This result is particularly significant given the recognized efficiency of $TiO_2$ as a photocatalyst. While hydroxylation of the $C_{60}$ cage is thought to reduce the net generation of singlet oxygen compared with the non-derivatized molecule, fullerol nonetheless appears to be a relatively powerful ROS producer. UFP also produced significant quantities of ROS, in contrast with the polystyrene particles that were inert (FIG. 7). A lack of ROS production by the PS particles is expected, as these particles are neither semiconductors nor photosensitizers. Although FFA does not differentiate between different ROS, supplementary techniques such as the use of electron spin trapping and quenchers such as superoxide dismutase (SOD) suggest that this assay measures multiple species.

Because the FFA assay does not assess speciation, nanobiosensor was used that is relatively specific for $H_2O_2$. Carbon nanotubes (CNTs) can be used to promote direct electron transfer from redox enzymes to an electrode surface and have shown great promise as biocompatible electrodes, capable of maintaining the functional properties of redox enzymes while linking biomolecules into nanoelectronic platforms including linking of glucose oxidase and NADH oxidase (Npx) to a CNT electrode array. In these systems, redox processes are detected as electronic signals that are registered by chronoamperometry and cyclic voltammetry. For the purposes of this study, a CNT-Npx bioelectrode that is capable of $H_2O_2$ detection with a high level of sensitivity was used Xia T, et al. Nano Lett 6:1794-807, 2006).

The formation of the Npx-gold electrode assembly and immobilization on the CNT array electrode was reported previously (Yeh J L, et al. Biosens Bioelectron 21:973-8, 2005; Withey G D, et al. Biosens Bioelectron 21:1560-5, 2006). Briefly, a three-electrode cell was used in the measurement: a Npx-bioassembly CNT array as the working electrode, and an Ag/AgCl reference electrode with a platinum wire as the counter electrode. Electrochemical measurements were performed on an Epsilon system (BASi) at 22° C. The bioelectrodes were equilibrated in the reaction buffer (acetate buffer, pH 6) or water, then scanned to obtain initial cyclic voltammograms (CV) of the enzyme assembly prior to sample measurements. Samples of $TiO_2$, fullerol, CB, and ultrafine particles were prepared by serially diluting with water to a final concentration of 50 pM and allowed to incubate 1 hr prior to measurements. Scans were taken at 1 hr (t=0) and at 1, 3, 7, 12, and 21 days at a scan rate of 100 mV/sec. Between sample analyses, all samples were tightly sealed and stored in the dark at 4° C. Prior to each measurement, the samples were slowly equilibrated to room temperature.

Figure 7B:
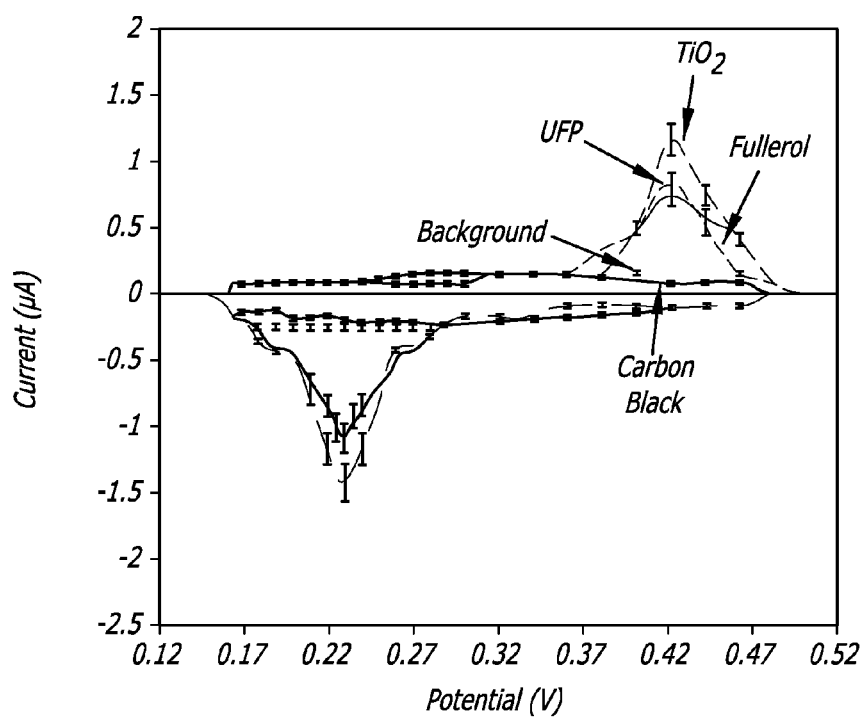
Figure 8A:
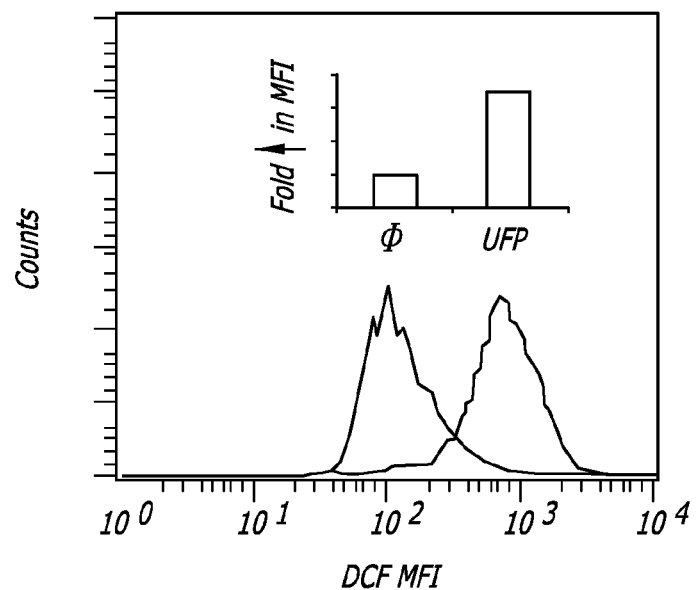
FIG. 8A-D depicts dichlorofluoroscein (DCF) fluorescence in RAW 264.7 cells treated with NP according to the teachings of the present invention. (A) Fold-increase in mean fluorescence intensity (MFI) in RAW 264.7 cells stained with DCF-DA, and treated with UFP for 4 hrs; (B) time course of $H_2O_2$ generation in response to UFP treatment; (C) effect of N-acetylcysteine (NAC) on UFP-induced $H_2O_2$ production at 4 and 16 hrs; and (D) comparison of the effect of UFP, fullerol, CB, $TiO_2$ and PS particles. *$p<0.01$, compared to control.
Figure 8B:
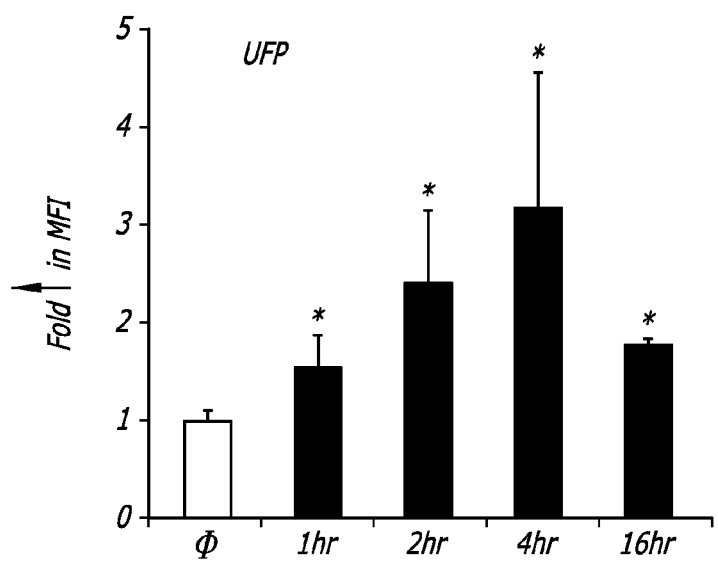
Figure 8C:
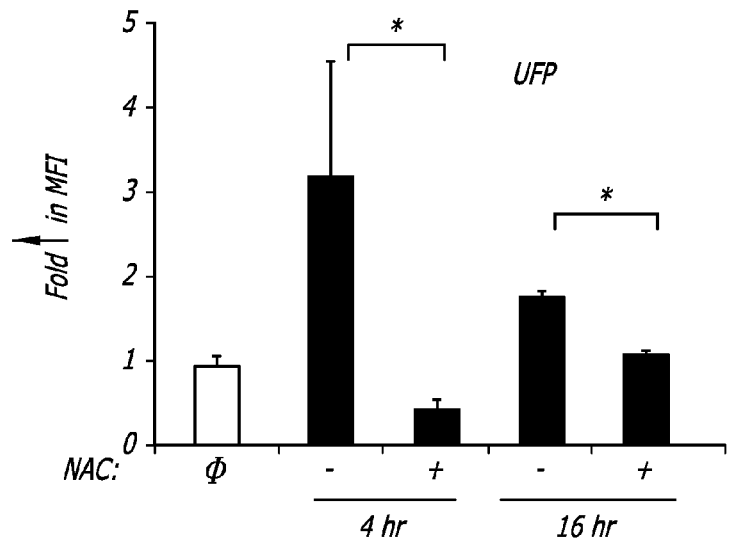
Figure 8D:
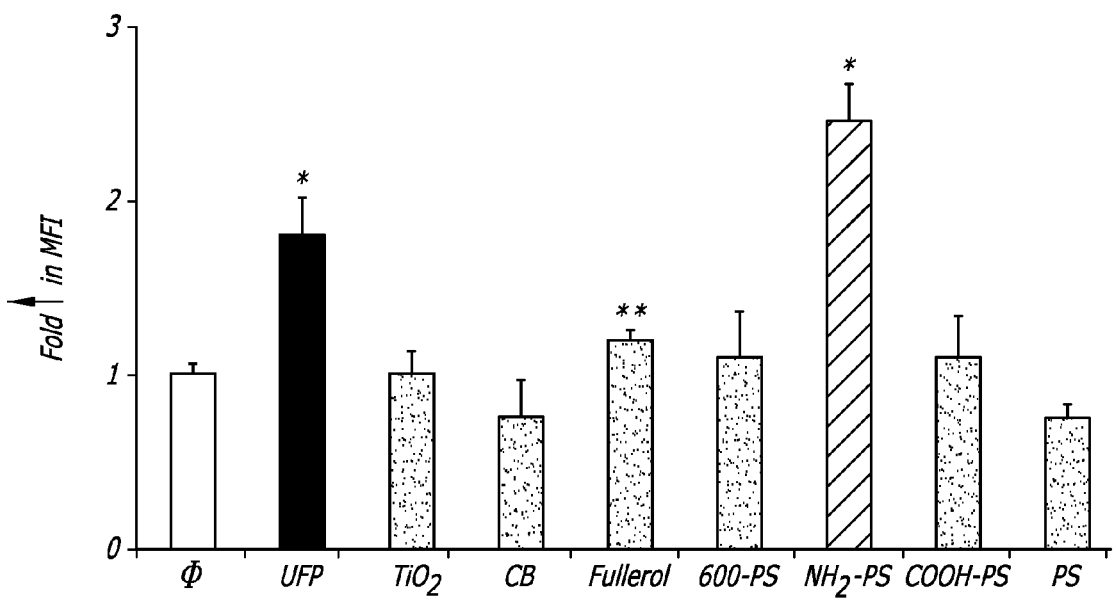

Introduction of NP to the CNT-Npx bioelectrode array demonstrated $H_2O_2$ generation by UFP, $TiO_2$, and fullerol samples (FIG. 7B). Similar to the FFA assay, $TiO_2$ generated the strongest signal, followed by UFP and then fullerol (FIG. 7). In contrast, CB and PS nanospheres showed little signal above baseline (CB alone is shown to avoid the data crowding; FIG. 7). The longevity of the oxidant signals was followed over three weeks (Table 7), with UFP, $TiO_2$, and fullerol exhibiting the potential for continuous oxidant generation over a time period of at least 7 days. These data show that some but not all NP are capable of spontaneous ROS generation.

TABLE 7

Time-dependent $H_2O_2$ production as assessed by the nanobiosensor

| Nanomaterial | Day 0 | Day 1 | Day 3 | Day 7 | Day 12 | Day 21 |
|---|---|---|---|---|---|---|
| UFP | ++ | ++ | ++ | ++ | + | − |
| $TiO_2$ | +++ | +++ | ++ | ++ | + | + |
| Fullerol | ++ | ++ | ++ | ± | − | 0 |
| Carbon Black | 0 | 0 | 0 | 0 | 0 | 0 |
| PS | 0 | 0 | 0 | 0 | 0 | 0 |

Example 3

Induction of ROS Production in RAW 264.7 Cells

RAW 264.7 cells were cultured in a 5% $CO_2$ in Dulbecco's Modified Eagle Medium (DMEM) containing 10% FCS, 5000 U/ml penicillin, 500 μg/ml streptomycin, and 2 mM L-glutamine (complete medium). For exposure to NP, aliquots of $3\times10^5$ cells were cultured in 24-well plates in 0.5 ml of medium at 37° C. for the indicated time periods. All the NP solutions were prepared fresh from stock solutions (10 mg/ml) and the solutions were sonicated for 10 sec before addition to cell cultures.

Cells were stained with the fluorescent dyes diluted in DMEM. The following dye combinations were added for 15-30 min at 37° C. in the dark: (i) 47.5 μg/ml propidium iodide (PI) in 200 μl DMEM (assessment of cell death); (ii) 20 nM $DiOC_6$ (assessment of Δψm); (iii) 2 μM MitoSOX™ red (superoxide generation) or 2 μM hydroethidine (HE, superoxide production); (iv) 2.5 μM 2,7 dichlorofluorescein (DCF, mostly assesses $H_2O_2$ production); (v) 5 μM Fluo-3 (assess cytoplasmic free calcium); (vi) 4 μM Rhod-2 (mitochondrial free calcium); (vii) 40 μM monobromobimane (MBB, assess intracellular thiol levels). Flow cytometry was performed using a FACScan (Becton Dickinson, Mountain View, Calif.) equipped with a single 488 nm argon laser. $DiOC_6$ and Fluo-3 fluorescence were analyzed in the FL-1 channel, while PI, Rhod-2 and MitoSOX red fluorescence were analyzed in FL-2. HE fluorescence was analyzed using FL-3 channels. Monobromobimane fluorescence was excited by the UV laser tuned to 325 nm, and emission was measured at 510 nm (FL-4 channel) in the LSR flow cytometer. Forward and side scatter were used to gate out cellular fragments.

Generation ROS by NP was detected in macrophages by using the fluorescent dyes DCFH-DA and MitoSOX™ Red (FIGS. 8 and 9). DCFH-DA is a non-polar compound that readily diffuses into cells, where it is hydrolyzed to the nonfluorescent polar derivative, DCFH, which becomes trapped in the cell. In the presence of a $H_2O_2$ and hydroxyl (OH.) radicals, DCFH is oxidatively modified into a highly fluorescent derivative DCF. The fold-increase in mean fluorescence intensity (MFI) of DCF was expressed as the ratio of particle-treated vs. control cells (FIG. 8A). Increased DCF fluorescence commenced within less than 1 hr of the addition of UFP and then continued to increase for 4 hours before beginning to decline (FIG. 8B). Pretreatment of the cells with the thiol antioxidant, N-acetylcysteine (NAC), significantly suppressed $H_2O_2$ production at 4 and 16 hrs (FIG. 8C). This is in agreement with previous studies showing that the redox cycling organic chemicals that are present on the UFP surface are directly neutralized by NAC. NAC also acts as a radical scavenger and precursor of glutathione (GSH) synthesis. In the testing of manufactured NP, only the cationic PS nanospheres induced an effect of similar magnitude (p<0.01) as UFP (FIG. 8D). NAC effectively disrupted the ROS production by $NH_2$-PS particles, suggesting that these particles engage in a thiol-dependent biological reaction. Fullerol generated a small but statistically significant (p<0.05) increase in DCF fluorescence (FIG. 8D).

Figure 9A:
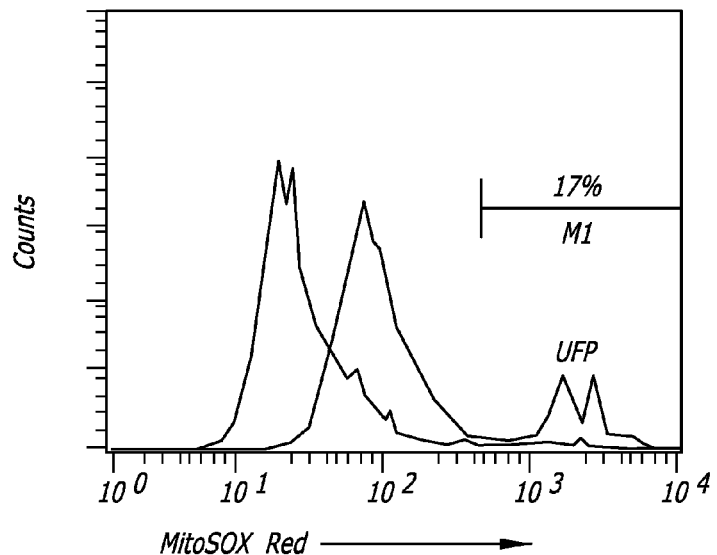
FIG. 9A-D depict mitochondrial $O_2.^-$ production in RAW 264.7 cells after treatment with NP according to the teachings of the present invention. (A) Generation of bright-positive (M1-gated) cells obtained by staining of RAW 264.7 cells with MitoSOX™ Red and treatment with UFP for 12 hr; (B) percent M−1 gated cells at 12 hr after treatment with UFP, fullerol, CB, $TiO_2$ or PS particles; (C) time course of increased MitoSOX™ fluorescence in cells treated with UFP or $NH_2$-PS; and (D) effect of NAC on cells treated with UFP or $NH_2$-PS for 16 hrs. *$p<0.01$, compared to control.
Figure 9B:
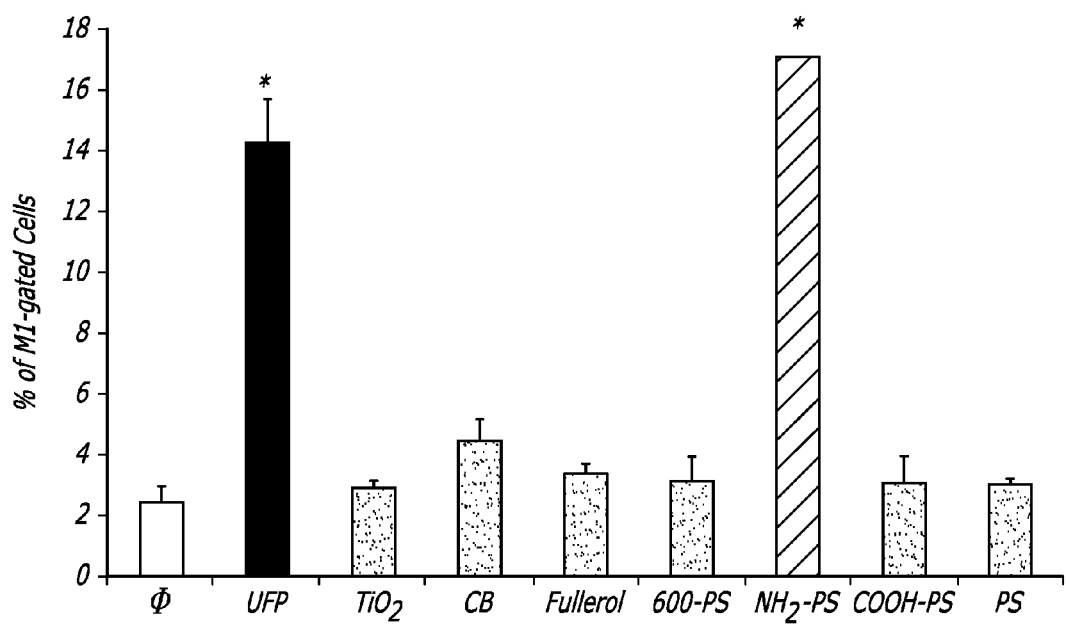
Figure 9C:
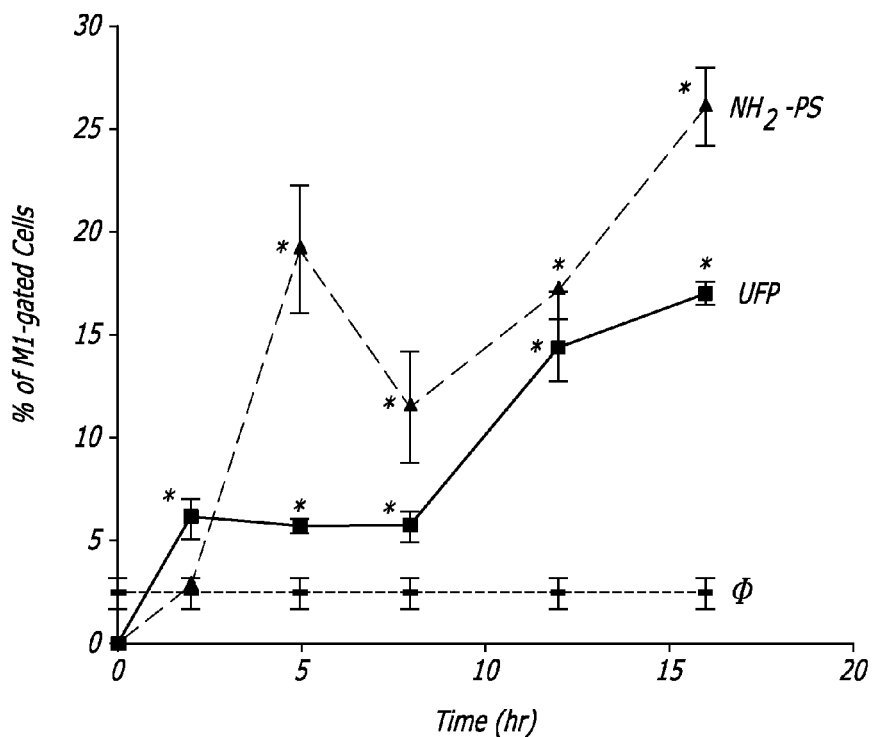
Figure 9D:
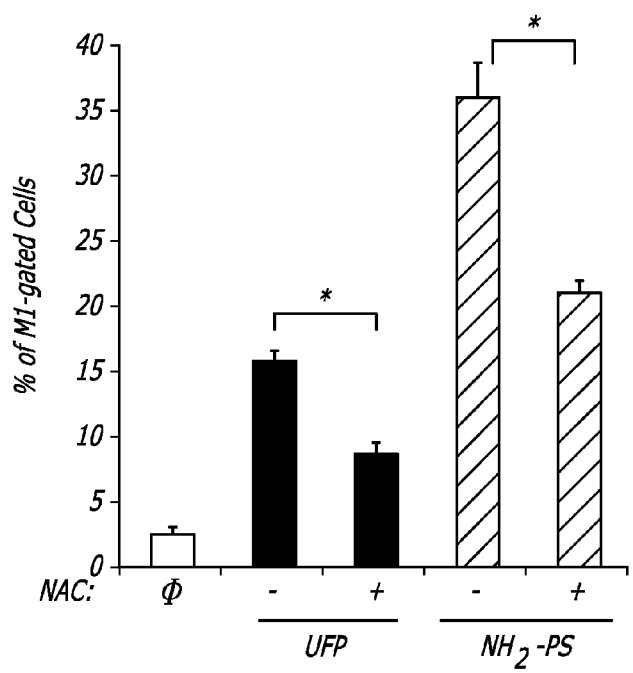
Figure 10:
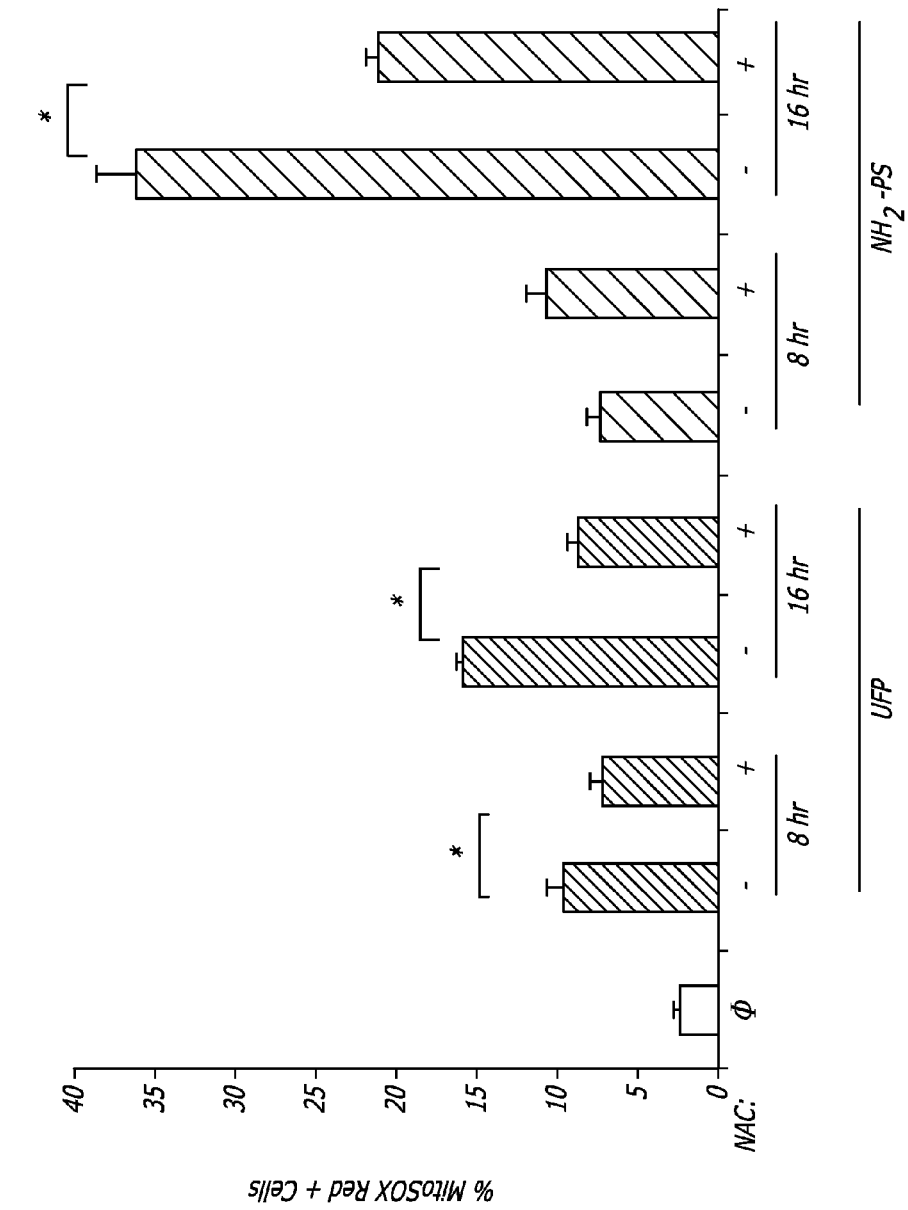
FIG. 10 depicts mitochondrial superoxide production in RAW 264.7 cells after treatment with nanoparticles according to the teachings of the present invention. *$p<0.01$, compared to control.

MitoSOX™ Red (Invitrogen, Carlsbad, Calif.) is a novel fluorogenic indicator offering direct measurement of superoxide ($O_2.^-$) production in live cells. This cell-permeant dye is rapidly and selectively concentrated in mitochondria, where oxidation by $O_2.^-$ but not other oxygen or nitrogen species, leads to the formation of a fluorescent product that interacts with nucleic acids. UFP exposure leads to a significant increase in the percentage of bright (M1)-fluorescent cells (FIG. 9A), as well as an increase in MFI. This increase commenced in less than 2 hr and remained stable for 8 hr, whereupon a sudden acceleration in the rate of $O_2.^-$ production leads to a progressive increase in fluorescent intensity for up to 16 hrs (FIG. 9C). Compared to UFP, all commercial NP were inactive except for the $NH_2$-PS nanospheres (FIG. 9B). These nanospheres generated a biphasic ROS response (FIG. 9C). The first peak reached its maximum at 5 hr, followed by a decline and then a progressive increase at greater than 8 hr (FIG. 9C). Interestingly, NAC could interfere in UFP-induced $O_2.^-$ generation at all time points, but had different effects on $NH_2$-PS responses at 8 hr and 16 hr time points (FIGS. 9D and 10). Thus, while NAC failed to suppress the ROS response at 8 hrs, it did interfere in the $NH_2$-PS response at 16 hrs (FIGS. 9D and 10). Essentially similar results were obtained when HE, a cell-permeant probe that is converted to bright-red ethidium bromide by $O_2.^-$, was used instead of MitoSOX™ red.

UFP participate in spontaneous and cell-mediated ROS production however, among the manufactured NP, only fullerol could mimic these actions. In spite of being the most active material under abiotic conditions, $TiO_2$ did not generate ROS in cells. Conversely, $NH_2$-PS nanospheres that are incapable of spontaneous ROS production, yet are potent inducers of $H_2O_2$ and $O_2.^-$ generation at a cellular level.

Example 4

Figure 11A:
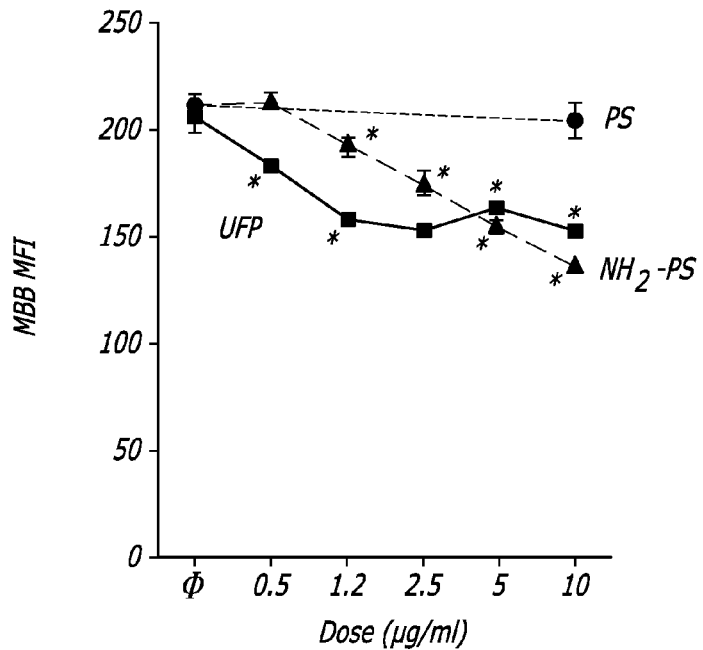
FIG. 11A-B depicts intracellular thiol levels in response to NP treatment in RAW 264.7 cells according to the teachings of the present invention. (A) MFI in monobromobimane (MBB)-stained RAW 264.7 cells following treated with the indicated amount of the particles for 16 hr; (B) time course of the change in MBB fluorescence in cells exposed to the indicated particles. *$p<0.01$, compared to control.
Figure 11B:
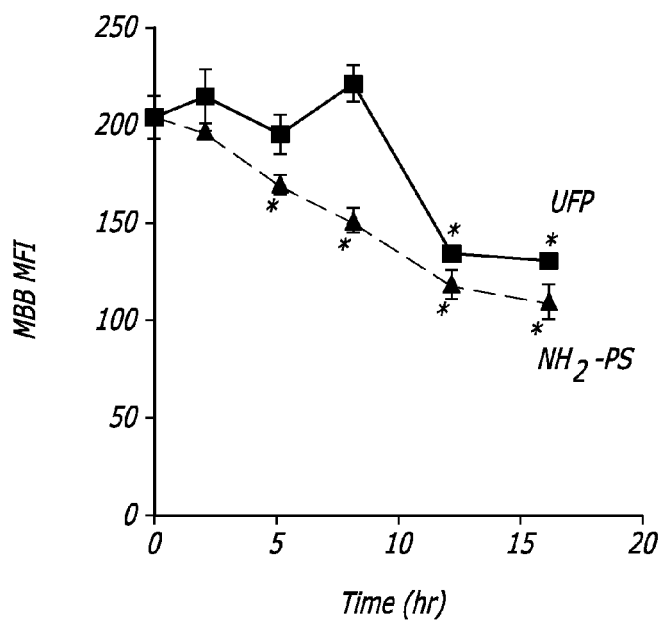

UFP and $NH_2$-PS Nanospheres are Capable of Inducing Oxidative Stress as Reflected by GSH Depletion and Heme Oxygenase 1 (HO-1) Expression Whether a biological response will follow ROS production is dependent on the magnitude of the response as well as the antioxidant defense capability of the cell. The GSH content of the cell in comparison to the GSSG value acts as a sensor that elects further cellular responses. Cellular thiol levels can be assessed with a thiol-interactive fluorescent dye, monobromobimane (MBB). While treatment with UFP and NH2-PS nanospheres induced a dose-dependent decline in MBB fluorescence, CB, TiO2, fullerol, and other forms of PS nanospheres had no effect (FIG. 11A). The kinetics of the UFP and $NH_2$-PS responses differ. While UFP failed to cause thiol depletion for up to 8 hours, $NH_2$-PS induced a more rapid and linear rate of decline (FIG. 11B), suggesting different biological mechanisms of action.

Figure 12A:
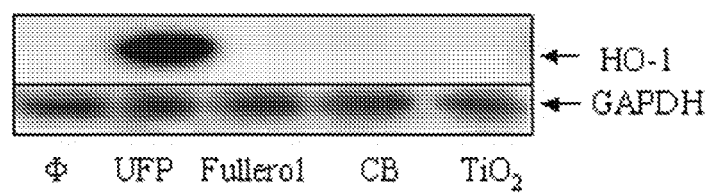
FIG. 12A-C depicts the induction of HO-1 expression according to the teachings of the present invention. RAW 264.7 cells were treated with each individual NP for 16 hrs before cellular extraction and immunoblotting. (A) Comparison of the effects of UFP with fullerol, CB, and $TiO_2$; (B) comparison of the effects of UFP with PS nanospheres; (C) effects of NAC on HO-1 expression. The lower panel in each blot shows equal protein loading as determined by glyceraldehyde-3-phosphate dehydrogenase (GAPDH) immunoblotting.
Figure 12B:
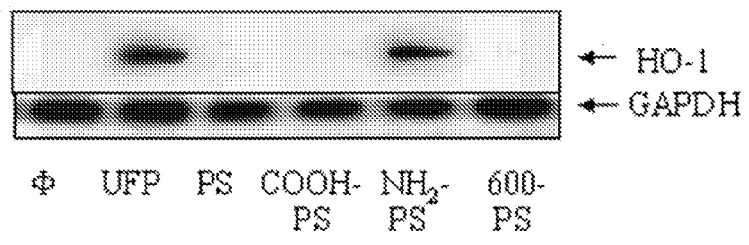
Figure 12C:
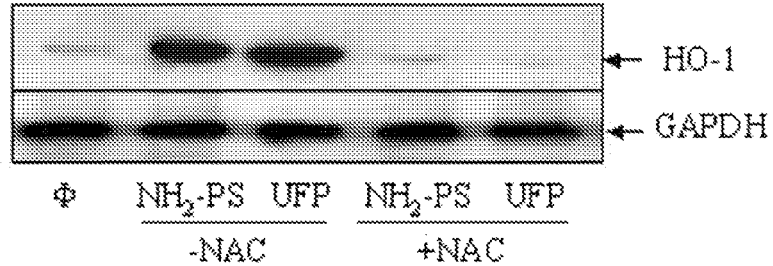
Figure 13A:
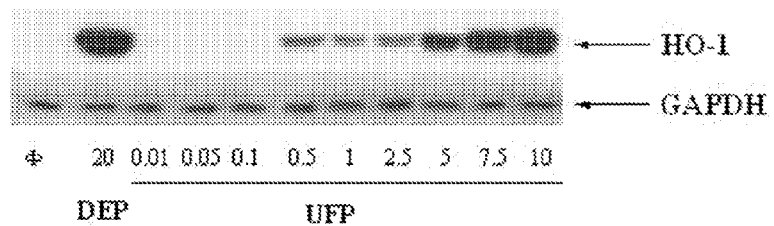
FIG. 13A-C depicts the effects NP on HO-1 expression and TNF-α production according to the teachings of the present invention. (A) Dose dependent HO-1 expression in RAW 264.7 cells exposed to UFP; (B) dose dependent TNF-α production in RAW 264.7 cells exposed to UFP; (C) TNF-α cytokine production in RAW 264.7 cells after exposure to LPS or UFP for 6 hr in the absence or presence of Polymixin B (PMB).

According to the hierarchical oxidative stress hypothesis, cells respond to even minimal levels of oxidative stress with a protective antioxidant response. This pathway is dependent on transcriptional activation of phase II gene promoters by the transcription factor Nrf2. HO-1 is a prime example of a phase II enzyme that mediates antioxidant, anti-inflammatory and cytoprotective effects, and is useful as a marker for particle-induced oxidative stress. Using an immunoblotting approach to assess HO-1 expression, both UFP and $NH_2$-PS nanospheres could be seen to elicit a response, while fullerol, CB, $TiO_2$ and other PS nanoparticles were ineffective (FIGS. 12A-B). The effect of UFP is dose-dependant (FIG. 13A). GAPDH immunoblotting was used to ascertain equal protein loading (lower panels). These data indicate that UFP and $NH_2$-PS are capable of generating biologically relevant oxidative stress effects. The induction of HO-1 expression was suppressed by NAC (FIG. 12C). These data demonstrate that some but not all NP are capable of generating oxidative stress under biological conditions.

Example 5

Jun Kinase Activation and TNF-α Production as a Reflection of Pro-Inflammatory Responses When antioxidant defenses fail to restore redox equilibrium, escalation in the level of oxidative stress could lead to cellular injury. One mechanism is the activation of pro-inflammatory cascades. The Jun kinase (JNK) and NF-kappa B cascades are redox-sensitive signaling cascades that are capable of inducing the expression of pro-inflammatory cytokines and chemokines, e.g., TNF-α.

Triplicate aliquots of RAW 264.7 cells were exposed to NP for 6 hr. The culture media were collected, centrifuged to remove all debris and the resultant supernatant assayed by ELISA for TNF-α and Western blotting for Jun kinase.

For Western blotting, 100 µg of total protein was separated by 10% SDS-PAGE and transferred to a PVDF membrane. After blocking, the membranes were incubated with primary antibodies against HO-1, phospho-JNK or JNK. The membranes were overlayed with secondary antibody before the addition of the HRP-conjugated avidin-biotin complex. The proteins were detected using ECL reagent according to the manufacturer's instructions. Protein abundance was quantified by densitometric scanning using a laser Personal Densitometer SI and Image Quant software (Amersham Biosciences).

Figure 13B:
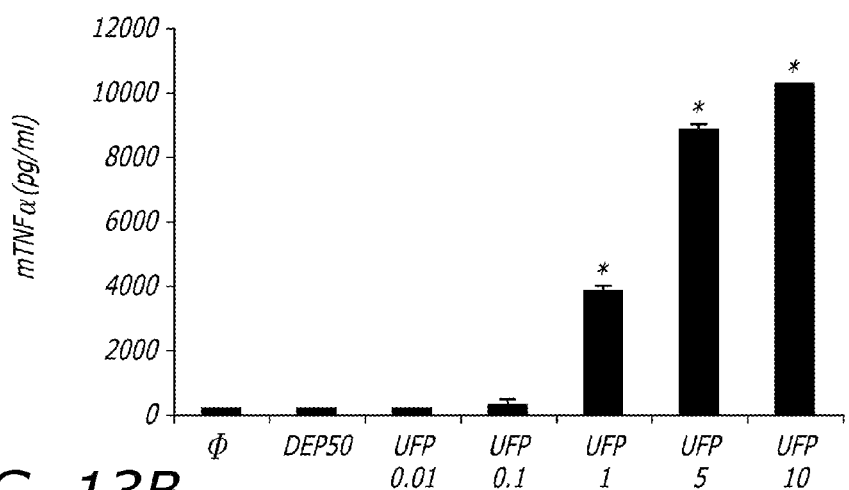
Figure 13C:
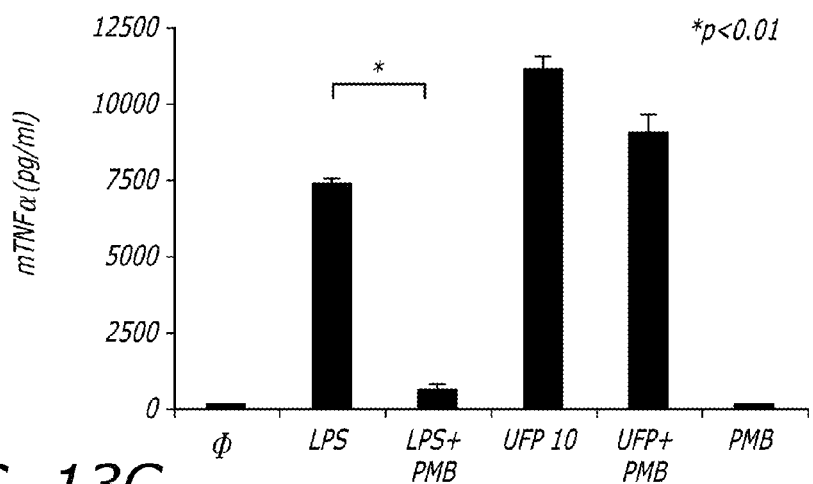
Figure 14A:
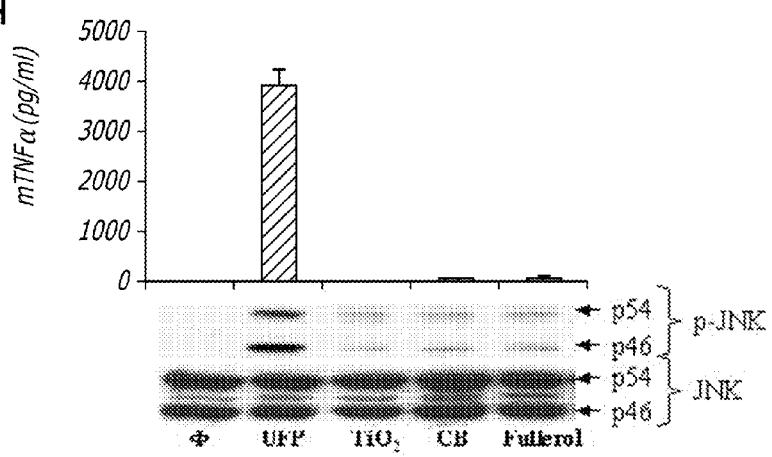
FIG. 14A-C depicts Jun kinase activation and TNF-α production by ELISA and immunoblotting in response to NP according to the teachings of the present invention. (A) ELISA and immunoblotting results comparing UFP with fullerol, CB, and $TiO_2$; (B) comparison of UFP with PS nanospheres; (C) RAW 264.7 cells pre-treated with NAC and sulforaphane (SFN) for 2 and 4 hr, respectively, before the addition of UFP for an additional 6 hr (supernatants were harvested to measure TNF-a levels by ELISA and the inserted immunoblot shows the effect of SFN on HO-1 expression). *$p<0.01$, compared to control.
Figure 14B:
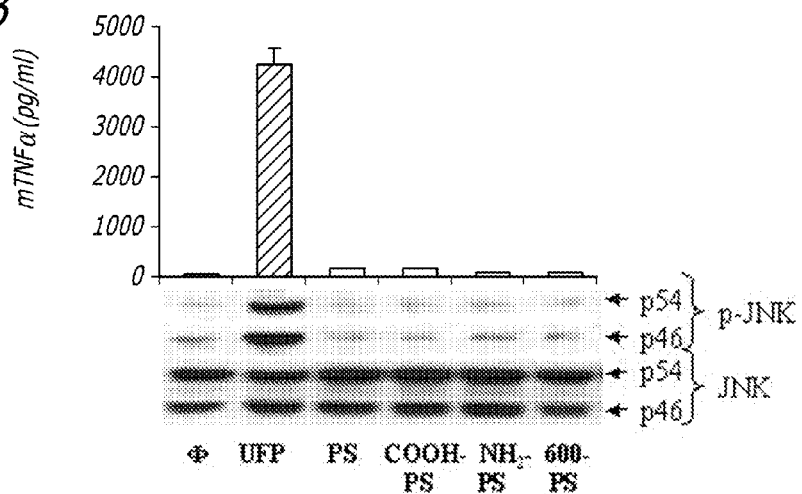

Among the NP, only the UFP were capable of JNK activation and TNF-α production (FIGS. 13 and 14A-B). This response was dose-dependent (FIG. 13B). Polymyxin B (PMB) was included in the assay to rule out possible endotoxin effects on TNF-α production (the UFPs contained a small amount, 20 U/ml, endotoxin). Thus, while PMB was capable of a significant suppression of the LPS-induced response, it had a small effect on the UFP response (FIG. 13C). None of the manufactured NPs contained any measurable (<0.1 U/ml) endotoxin levels. Therefore endotoxin contamination was not responsible for the pro-inflammatory effect of the NPs. Despite their ability to generate ROS, $NH_2$-PS nanospheres were ineffective inducers of JNK activation or cytokine production (FIG. 14B). This supports the notion that these particles operate via different mechanisms.

Figure 14C:
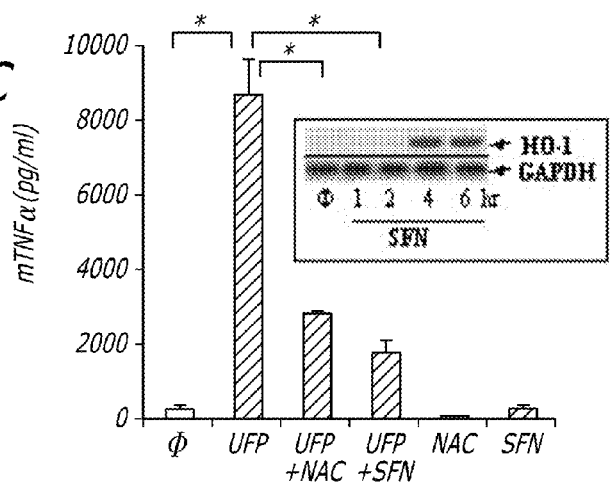

In order to demonstrate the dynamic relationship between protective and pro-inflammatory cellular responses, the effect of increased of phase II enzyme expression was investigated on the UFP-induced responses (FIG. 14C). Sulforaphane (SFN) is an electrophilic chemical that is capable of transcriptional activation of phase II gene promoters without inducing overt toxicity. Prior treatment of RAW 264.7 cells with SFN resulted in HO-1 expression and interference in TNF-α production (FIG. 14C, insert). HO-1 is a representative phase II enzyme. Subsequent addition of UFP led to a blunted TNF-α response (FIG. 14C). NAC was also capable of interfering in UFP-induced TNF-α production for reasons discussed earlier on (FIG. 14C).

Example 6

NP Increase Cellular and Mitochondrial Calcium ($Ca^{2+}$) Levels

Figure 15A:
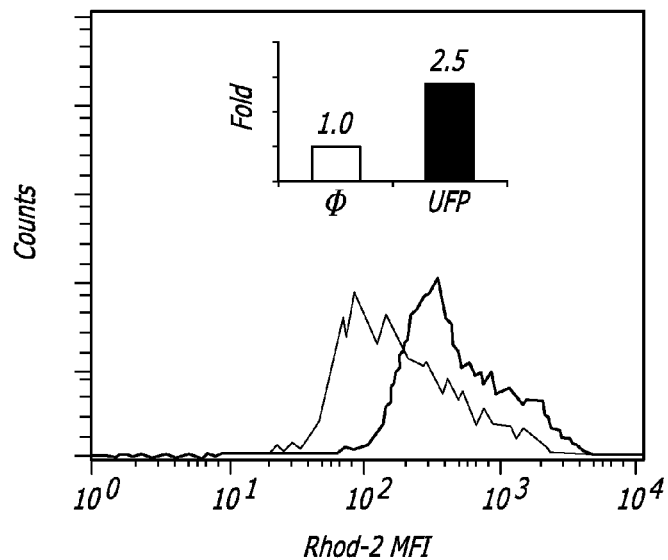
FIG. 15A-B depicts the effect of NP on mitochondrial calcium levels, $[Ca^{2+}]_m$ according to the teachings of the present invention. (A) Fold-increase in MFI in RAW 264.7 cells incubated with Rhod-2 for 0.5 hr after the addition of UFP for 16 hr; (B) comparison of the MFI of cells treated with UFP, fullerol, CB, $TiO_2$ and PS nanospheres for 16 hr. *$p<0.01$ or **$p<0.05$, compared to control.
Figure 15B:
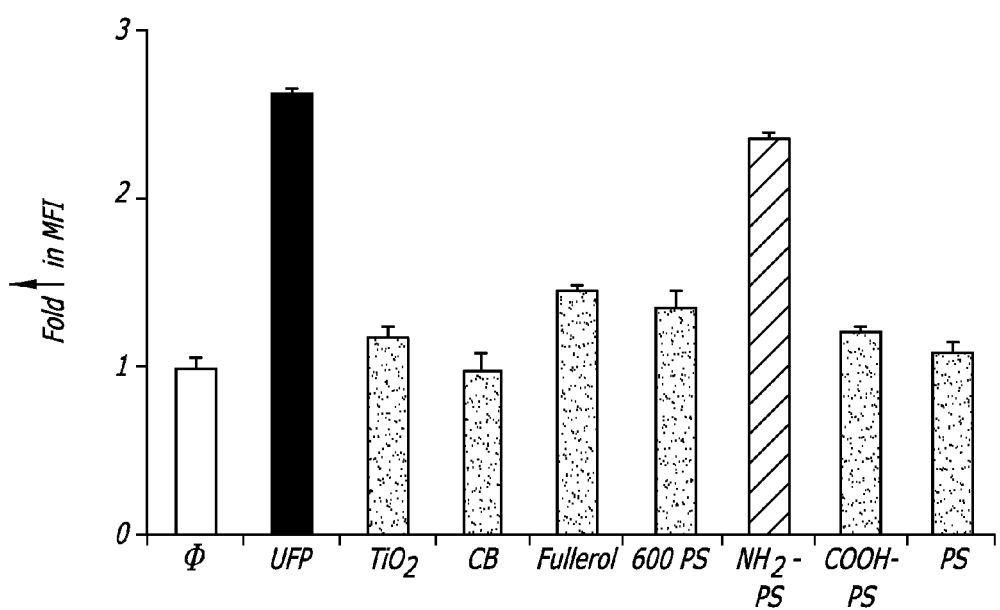
Figure 16:
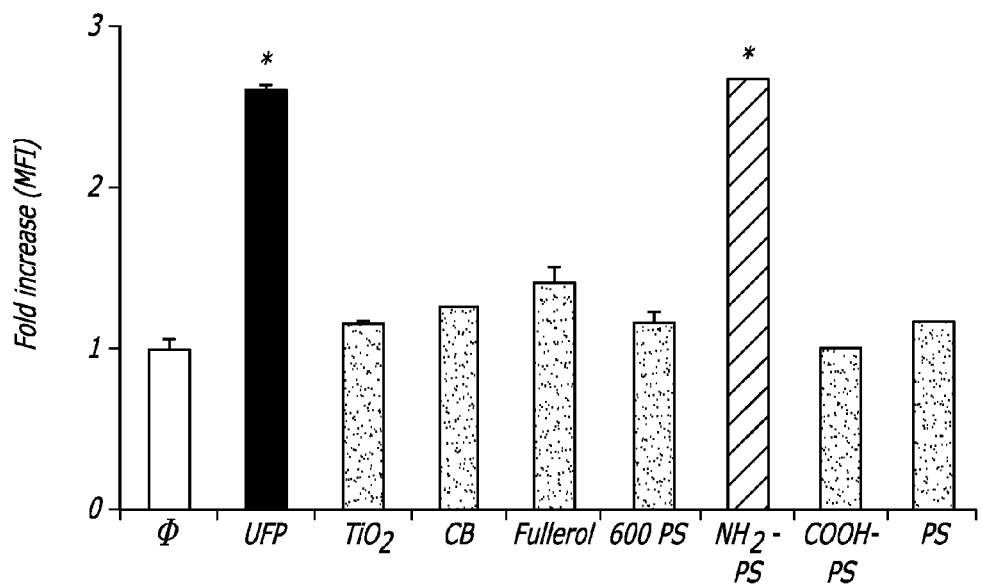
FIG. 16 depicts the effects of NP on $[Ca^{2+}]_i$ as measured by Fluo-3 according to the teachings of the present invention. *$p<0.01$, compared to control.

Oxidative stress can induce changes in the intracellular free calcium concentration, $[Ca^{2+}]_i$, or may perturb $Ca^{2+}$ compartmentalization, with the potential of inducing cellular toxicity. Mitochondrial $Ca^{2+}$ levels, $[Ca^{2+}]_m$, were followed by treating Rhod-2 stained cells with NP (FIG. 15A). UFP exposure induced a significant increase in Rhod-2 fluorescence starting at 4 hr; this increase is progressive, culminating in a 2.5-fold increase by 16 hr (FIG. 15A). When repeated with manufactured NP, only the amino-modified PS nanospheres exerted a comparable (2-fold) effect; fullerol generated a smaller yet still statistically significant increase (FIGS. 15A-B). The intimate relationship of $[Ca^{2+}]_m$ and $[Ca^{2+}]_i$ was further demonstrated with Fluo-3. Cellular staining with this fluorescent dye, which reflects $[Ca^{2+}]_i$, yielded almost identical effects as Rhod-2 (FIG. 16). These data demonstrate that particle-generated oxidative stress influence cellular and mitochondrial function via a $Ca^{2+}$-regulated pathway that has a recognized link to cytotoxicity.

Example 7

Electron Microscopy Reveals NP Uptake and Mitochondrial Damage

Detailed investigation of nanomaterial toxicity should consider NP uptake and subcellular localization. Mitochondria have been identified as a possible target for UFP, fullerene derivatives and micellar nanocontainers.

Electron microscopy was performed as previously described (Yang A H, et al., In Vitro Cell Dev Biol 23:34-46, 1987). Thin sections were cut with a Reichert-Jung ultracut and ultramicrotome (Leica, Stuttgart, Germany). Copper grids were stained with lead citrate and uranyl acetate and photographed in a Hitachi electron microscope (Hitachi Instrument Inc., Tokyo, Japan). The TEM of NP was performed after drying up particle solutions on 400 mesh grids, then analyzed by a JEOL 100CX transmission electron microscope.

Electron microscopy (EM) analysis of RAW 264.7 cells demonstrated mitochondrial swelling within less than 4 hr of the addition of UFP. This was followed by loss of cristae and the appearance of intracellular vacuoles that contain electron dense material (FIG. 17B). These changes were progressive, ultimately resulting in large particle-filled vacuoles and disappearance of mitochondria (FIG. 17B). In contrast, $TiO_2$ particles were taken up into loose-fitting phagosomes without noticeable mitochondrial damage (FIG. 17C). Similarly, CB particles were taken up in phagosomes without mitochondrial damage. With regard to fullerol uptake, approximately 10% of cells showed electron dense clumps that appear not to be membrane bound (FIG. 17D). Mitochondria remained intact in greater than 95% of these cells.

Figures 17E, 17F:
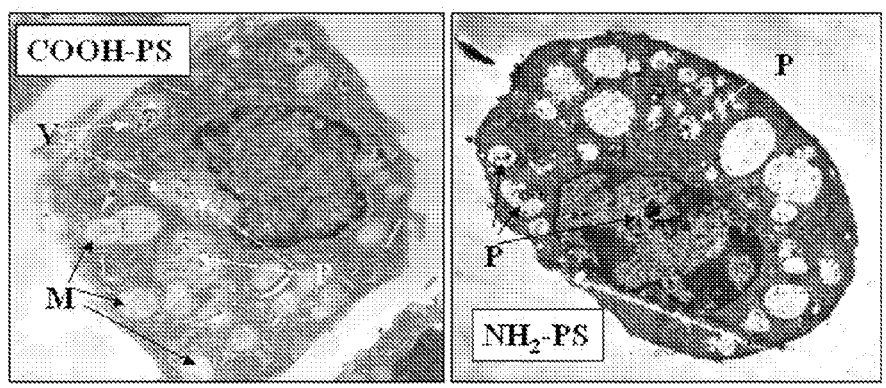

Anionic and cationic PS nanospheres induced contrasting morphological changes. Carboxylated-NP were taken up in loose-fitting phagosomes, with preservation of mitochondria architecture (FIG. 17E). In contrast, $NH_2$-PS nanospheres could be seen to collect in large membrane-bound vacuoles and the nuclei of cells that showed disappearance of mitochondria (FIG. 17F). This suggests that the cationic particles could enter an endocytic compartment that targets mitochondria, similar to UFP. Sixty nm PS particles and 600 nm $NH_2$-PS particles did not exhibit noticeable cellular uptake or damage.

Example 8

NP Exerts Functional Effects on Mitochondria and Induces Cellular Toxicity

Figure 18E:
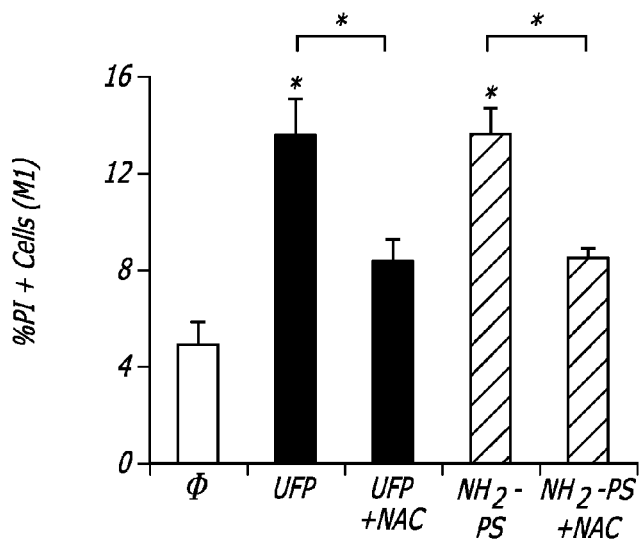
FIG. 18A-E depict changes in mitochondrial membrane potential (Δψm) and cellular toxicity (PI uptake) during NP exposure according to the teachings of the present invention. Cells were treated with UFP or manufactured NP for 16 hrs before staining with $DiOC_6$. (A) $DiOC_6$ fluorescence in response to UFP treatment representing a decline in Δψm (the M1 bar was used to score the % of $DiOC_6$lo cells); (B) comparison of the percent $DiOC_6$lo cells 16 hrs following the addition of UFP, fullerol, CB, $TiO_2$ or PS nanospheres; (C) propidium iodide (PI) uptake in RAW 264.7 cells treated with UFP for 16 hrs (M1 gating was used to assess the percent $PI^+$ cells, which represent cells that are extensively damaged); (D) $PI^+$ cells after treatment with UFP, fullerol, CB, $TiO_2$ and PS nanospheres for 16 hrs; (D) effect of NAC on cytotoxicity by UFP and 60 nm $NH_2$-PS particles. *$p<0.01$, NAC treated versus non-NAC treated samples; (E) effect of NAC on cytotoxicity of UFP and $NH_2$-PS particles.
Figure 18A:
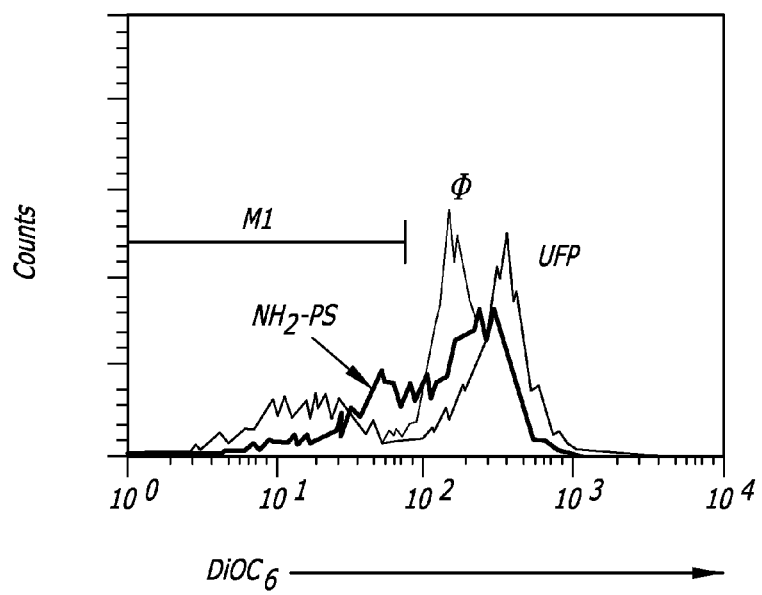
Figure 18B:
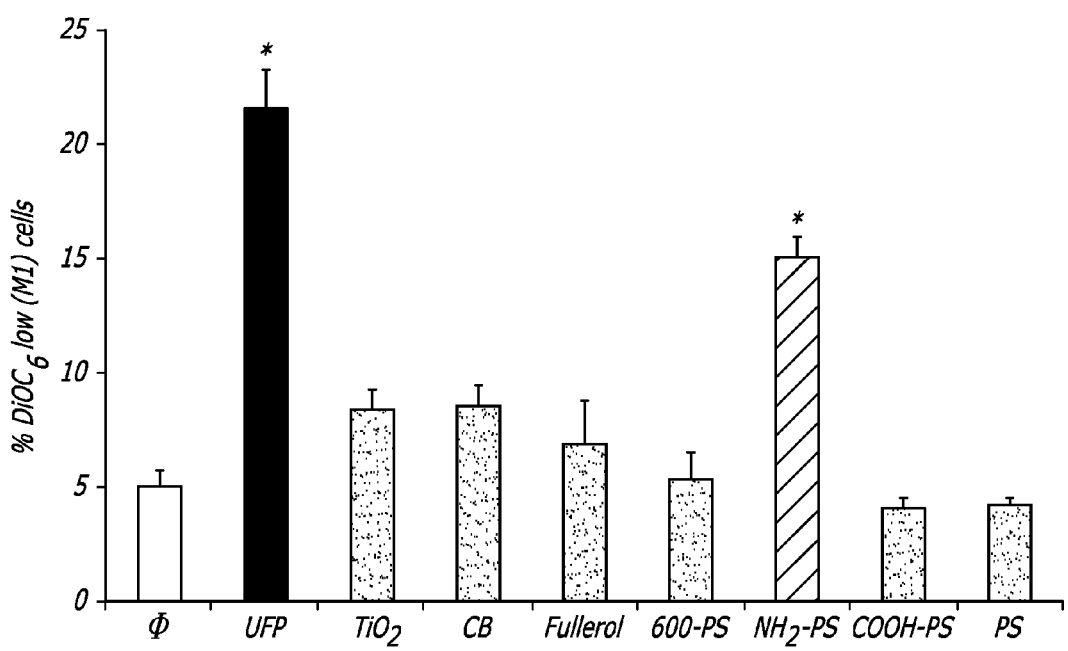

Toxic oxidative stress can perturb mitochondrial function in a number of ways, including disruption of electron flow in the inner membrane, dissipation of the mitochondrial membrane potential ($\Delta\psi m$), mitochondrial $Ca^{2+}$ uptake, and large-scale opening of the PTP. These changes can be followed by using fluorescent dyes that are tracked in a flow cytometer. $DiOC_6$ is a cationic dye that is highly concentrated in the negatively charged mitochondrial matrix. Dissipation of the $\Delta\psi m$ leads to the $DiOC_6$ release and decreases cellular fluorescence as seen during treatment with UFP and $NH_2$-PS (FIG. 18A). These changes commence at 1 hr of the addition of the UFP, but require a longer incubation period (>6 hr) upon addition of $NH_2$-PS. Compared to the effects of UFP and $NH_2$-PS, fullerol, CB, $TiO_2$, and other PS particles failed to exert an influence on the $\Delta\psi m$ (FIG. 18B).

Figure 18C:
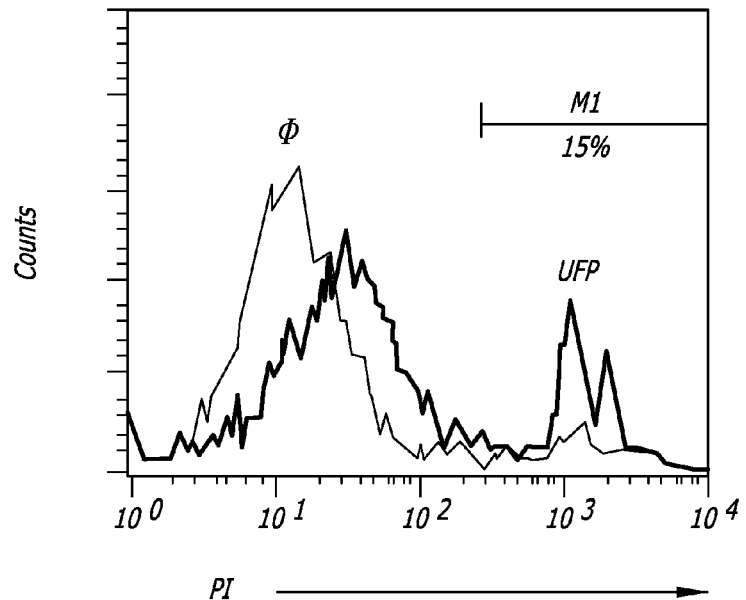
Figure 18D:
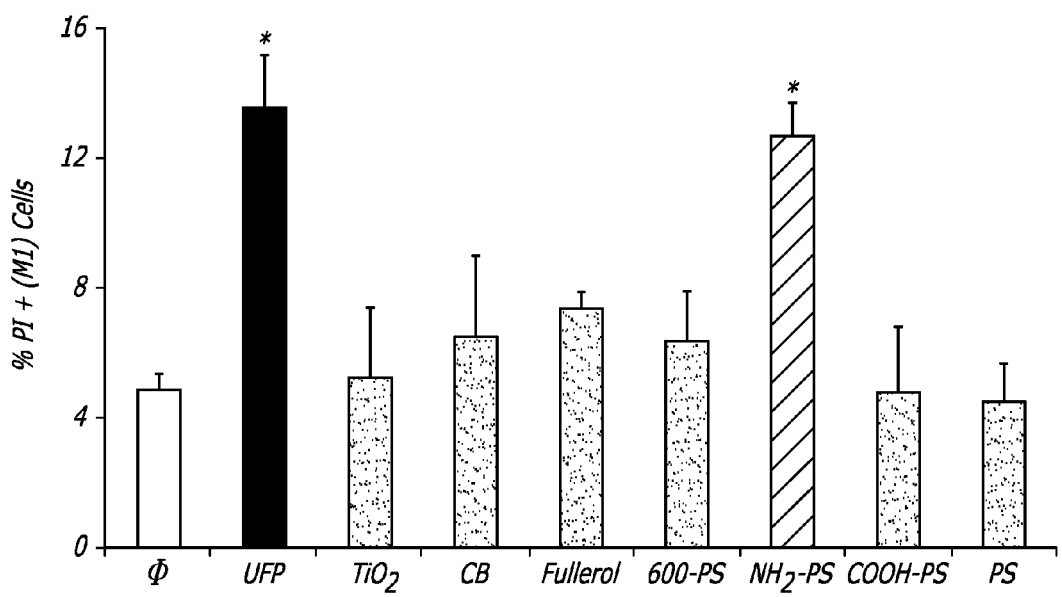

Large-scale PTP opening leads to mitochondrial depolarization, $O_2.^-$ production and the release of pro-apoptotic factors. Cellular toxicity was assessed by PI staining (FIG. 18C). UFP induced a dose-dependent increase in PI uptake in the nuclei of damaged cells; these changes commenced at a particle dose of 0.5 µg/ml. Compared to the statistically significant increase in PI fluorescence with UFP, $TiO_2$, CB, and fullerol were inactive (FIG. 18D). Among the PS particles, only the $NH_2$-nanospheres induced a significant increase in the percentage of PI-positive cells (FIG. 18D). NAC could interfere in the cytotoxicity of UFP and $NH_2$-PS (FIG. 18E).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Of course, variations on those embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An in vitro method of predicting the toxicity of nanomaterials in subjects exposed to nanomaterials, the method comprising the steps of:
   (a) providing a quantity of cells to an in vitro culture system, the in vitro culture system including a tissue culture medium;
   (b) adding thereto a quantity of nanomaterials;
   (c) maintaining said cells with the nanomaterials for a period of time; and
   (d) performing on said cells a plurality of in vitro assays including all of:
      (i) a reactive oxygen species (ROS) production assay;
      (ii) a phase II antioxidant molecule expression assay;
      (iii) a proinflammatory cascade activation assay;
      (iv) a mitochondrial perturbation and apopotosis assay; and
      (v) an assay to determine cellular uptake and subcellular localization of the nanoparticles;
   wherein the results of said in vitro assays predict the toxicity of said nanomaterials in a subject exposed to the nanomaterials.

2. The method of claim 1, wherein said cells are selected from the group consisting of macrophages, epithelial cells, endothelial cells, keratinocytes, neuronal cells, kidney cells, liver cells, antigen presenting cells, and Salmonella bacterium cells.

3. The method of claim 2 wherein said cells are isolated from an organism selected from the group consisting of invertebrates, mammals, bacteria and yeast.

4. The method of claim 2 wherein said cells are freshly isolated.

5. The method of claim 2 wherein said cells comprise a cultured cell line.

6. The method of claim 1, wherein said cells are maintained in culture with said nanomaterials for a period of time extending from 1 hour to 4 weeks.

7. The method of claim 6 wherein said cells are maintained in culture with said nanomaterials for a period of time extending from 1 hour to 24 hours.

8. The method of claim 1, wherein said assay for ROS production comprises measuring levels of reduced and oxidized glutathione of said cells.

9. The method of claim 1, wherein said assay for ROS production comprises detecting the presence of superoxide or $H_2O_2$ radicals in said cells, as well as in said tissue culture medium.

10. The method of claim 1, wherein said assay for ROS production comprises measuring levels of reduced and oxidized glutathione in said cells and detecting the presence of superoxide or $H_2O_2$ radicals in said cells.

11. The method of claim 1, wherein said phase II antioxidant molecule is at least one molecule selected from the group consisting of heme oxygenase 1 (HO-1), catalase, superoxide dismutase, glutathione-S-transferase, glutathione peroxidase, glutathione reductase, and thioredoxin reductase.

12. The method of claim 1, wherein said assay for phase II antioxidant molecule expression comprises measuring levels of antioxidant proteins in said cells.

13. The method of claim 1, wherein said assay for phase II antioxidant molecule expression comprises measuring mRNA levels of antioxidant proteins in said cells.

14. The method of claim 1, wherein said assay for phase II antioxidant molecule expression comprises measuring levels of antioxidant proteins in said cells and measuring mRNA levels of the antioxidant proteins in said cells.

15. The method of claim 1, wherein proinflammatory cascades comprise MAP kinase and NF-kappa B cascades.

16. The method of claim 15 wherein said MAP kinases are selected from the group consisting of Jun kinase, ERK, and p38 MAP kinase.

17. The method of claim 15, wherein the NF-kappa B cascade comprises I kappa B kinases, I kappa B protein, and NF-kappa B transcription factors.

18. The method of claim 15 wherein said assays for activation of said proinflammatory cascades comprise measuring phosphorylation status of MAP kinases in said cells.

19. The method of claim 1, wherein said assays for activation of said proinflammatory cascades comprises measuring activation of pro-inflammatory molecules selected from the group consisting of cytokines, chemokines, and adhesion molecules in the cells.

20. The method of claim 19, wherein said cytokines, chemokines, and adhesion molecules are selected from the group consisting of IL-8, IL-6, TNF-α, MCP-1, M-CSF, GM-CSF, RANTES, eotaxin, ICAM-1, VCAM-1, and other related products.

* * * * *

UNITED STATES PATENT AND TRADEMARK OFFICE
CERTIFICATE OF CORRECTION

| | | Page 1 of 1 |
|---|---|---|
| PATENT NO. | : 8,512,943 B2 | |
| APPLICATION NO. | : 12/095902 | |
| DATED | : August 20, 2013 | |
| INVENTOR(S) | : Andre E. Nel | |

It is certified that error appears in the above-identified patent and that said Letters Patent is hereby corrected as shown below:

In the Specification:

Col. 1, Lines 14-19

In the paragraph under Statement Regarding Federally Sponsored Research or Development, the paragraph should be changed to the following:

This invention was made with Government support under Grant No. R82735201 awarded by the Environmental Protection Agency and Grant Nos. AI050495, ES010553, and ES012053 awarded by the National Institutes of Health. The Government has certain rights in the invention.

Signed and Sealed this
Twenty-ninth Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,512,943 B2 | Page 1 of 1 |
| APPLICATION NO. | : 12/095902 | |
| DATED | : August 20, 2013 | |
| INVENTOR(S) | : Nel | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1145 days.

Signed and Sealed this
Twenty-seventh Day of January, 2015

Michelle K. Lee
*Deputy Director of the United States Patent and Trademark Office*